(12) United States Patent
Bakowski Holtryd et al.

(10) Patent No.: US 10,813,607 B2
(45) Date of Patent: Oct. 27, 2020

(54) X-RAY SENSOR, METHOD FOR CONSTRUCTING AN X-RAY SENSOR AND AN X-RAY IMAGING SYSTEM COMPRISING SUCH AN X-RAY SENSOR

(71) Applicant: PRISMATIC SENSORS AB, Stockholm (SE)

(72) Inventors: Mietek Bakowski Holtryd, Stillingsön (SE); Mats Danielsson, Täby (SE); Cheng Xu, Täby (SE)

(73) Assignee: PRISMATIC SENSORS AB, Stockholm (SE)

( * ) Notice: Subject to any disclaimer, the term of this patent is extended or adjusted under 35 U.S.C. 154(b) by 106 days.

(21) Appl. No.: 16/020,560

(22) Filed: Jun. 27, 2018

(65) Prior Publication Data

US 2020/0006409 A1 Jan. 2, 2020

(51) Int. Cl.
*A61B 6/00* (2006.01)
*A61B 6/03* (2006.01)
(Continued)

(52) U.S. Cl.
CPC ............ *A61B 6/4241* (2013.01); *A61B 6/035* (2013.01); *A61B 6/42* (2013.01); *A61B 6/4233* (2013.01); *A61B 6/4283* (2013.01); *A61B 6/44* (2013.01); *A61B 6/4429* (2013.01); *A61B 6/4435* (2013.01); *A61B 6/4441* (2013.01);
(Continued)

(58) Field of Classification Search
CPC ........... A61B 6/032; A61B 6/035; A61B 6/42; A61B 6/4208; A61B 6/4233; A61B 6/4241; A61B 6/4283; A61B 6/44; A61B 6/4429; A61B 6/4435; A61B 6/4441; A61B 6/4447; A61B 6/4452; A61B 6/482; G01T 1/24; G01T 1/241; G01T 1/249; H01L 27/14658; H01L 27/14659; G01N 23/046; G01N 23/18; G01N 23/083; G01N 23/087; G01V 5/0016; G01V 5/0041; G01V 5/005; G01V 5/0025
USPC ...... 378/19, 62, 98.8, 98.9, 98.11, 196–198; 250/370.09
See application file for complete search history.

(56) References Cited

U.S. PATENT DOCUMENTS 4,377,816 A 3/1983 Sittig
5,677,539 A * 10/1997 Apotovsky ............... G01T 1/24
250/370.13
(Continued)

FOREIGN PATENT DOCUMENTS

EP 0 661 753 A1 7/1995

*Primary Examiner* — Allen C. Ho
(74) *Attorney, Agent, or Firm* — Nixon & Vanderhye

(57) ABSTRACT

An X-ray sensor (1) having an active detector region including a plurality of detector diodes (2) arranged on a surface region (3) of the X-ray sensor (1), a junction termination (4) surrounding the surface area (3) including the plurality of detector diodes (2), the junction termination (4) including a guard (5) arranged closest to the end of the surface region (3), a field stop (6) arranged outside the guard (2) and a number N of field limiting rings, FLRs (7) arranged between the guard (5) and the field stop (6), wherein each of the FLRs (7) are placed at positions selected so that distances between different FLRs (7) and between the guard and the first FLR lie within an effective area, the effective area being bounded by the lines $\alpha=(10+1.3\times(n-1))$ μm and $\beta=(5+1.05\times(n-1))$ μm.

23 Claims, 18 Drawing Sheets

(51) Int. Cl.
*G01N 23/04* (2018.01)
*G01N 23/046* (2018.01)
*G01T 1/24* (2006.01)
*H01L 27/146* (2006.01)
*G01V 5/00* (2006.01)
*G01N 23/18* (2018.01)
*G01N 23/087* (2018.01)
*G01N 23/083* (2018.01)

(52) U.S. Cl.
CPC .......... *A61B 6/4447* (2013.01); *A61B 6/4452* (2013.01); *A61B 6/482* (2013.01); *G01N 23/046* (2013.01); *G01N 23/083* (2013.01); *G01N 23/087* (2013.01); *G01N 23/18* (2013.01); *G01T 1/24* (2013.01); *G01T 1/241* (2013.01); *G01T 1/249* (2013.01); *G01V 5/005* (2013.01); *G01V 5/0016* (2013.01); *G01V 5/0025* (2013.01); *G01V 5/0041* (2013.01); *H01L 27/1463* (2013.01); *H01L 27/14658* (2013.01); *H01L 27/14659* (2013.01); *H01L 27/14687* (2013.01); *A61B 6/032* (2013.01); *A61B 6/4078* (2013.01); *A61B 6/4085* (2013.01); *A61B 6/4208* (2013.01)

(56) References Cited

U.S. PATENT DOCUMENTS

| | | | | |
|---|---|---|---|---|
| 5,777,373 | A | 7/1998 | Groenig | |
| 5,905,264 | A * | 5/1999 | Shahar | H01L 27/14601 250/370.01 |
| 5,943,388 | A * | 8/1999 | Tümer | G01V 5/0041 378/98.11 |
| 5,952,646 | A * | 9/1999 | Spartiotis | G01T 1/24 250/208.1 |
| 6,002,134 | A * | 12/1999 | Lingren | H01L 27/14659 250/370.01 |
| 6,034,373 | A * | 3/2000 | Shahar | H01L 27/14676 250/338.4 |
| 6,037,595 | A * | 3/2000 | Lingren | G01T 1/241 250/370.01 |
| 6,380,528 | B1 * | 4/2002 | Pyyhtiä | H04N 5/232 250/208.1 |
| 6,509,203 | B2 * | 1/2003 | Spartiotis | H01L 27/14623 257/441 |
| 6,765,213 | B2 * | 7/2004 | Shahar | G01T 1/2928 250/370.01 |
| 6,794,654 | B1 * | 9/2004 | Hansen | H01L 27/14658 250/366 |
| 6,797,960 | B1 * | 9/2004 | Spartiotis | G01N 23/04 250/370.01 |
| 6,928,144 | B2 * | 8/2005 | Li | A61B 6/032 250/370.09 |
| 7,223,982 | B1 * | 5/2007 | Chen | G01T 1/2928 250/370.13 |
| 7,634,061 | B1 * | 12/2009 | Tümer et al. | G01T 1/247 378/62 |
| 7,796,722 | B2 * | 9/2010 | Janssen | G01T 1/2928 378/19 |
| 8,044,485 | B2 * | 10/2011 | Miyoshi | H01L 29/872 257/104 |
| 8,049,178 | B2 * | 11/2011 | Lynn | G01T 1/24 250/371 |
| 8,063,379 | B2 * | 11/2011 | Suhami | G01T 5/02 250/370.09 |
| 8,093,624 | B1 | 1/2012 | Renzi et al. | |
| 8,159,049 | B2 * | 4/2012 | Hietanen | H01L 23/481 257/432 |
| 8,165,266 | B2 * | 4/2012 | Wear | A61B 6/4042 250/370.13 |
| 8,237,126 | B2 * | 8/2012 | Von Känel | H01L 27/14659 250/338.4 |
| 8,471,293 | B2 * | 6/2013 | Sanfilippo | H01L 27/1446 257/186 |
| 8,476,101 | B2 * | 7/2013 | Chen | H01L 31/02966 257/448 |
| 8,563,936 | B2 * | 10/2013 | Bruzzi | G01T 1/026 250/361 R |
| 8,921,797 | B2 * | 12/2014 | Kostamo | G01T 1/2928 250/370.14 |
| 9,087,755 | B2 * | 7/2015 | Frach | H01L 27/1443 |
| 9,129,939 | B2 * | 9/2015 | Imai | H01L 29/45 |
| 9,224,802 | B2 * | 12/2015 | Hiyoshi | H01L 29/66068 |
| 9,224,877 | B2 * | 12/2015 | Hiyoshi | H01L 29/872 |
| 9,276,105 | B2 * | 3/2016 | Yamada | H01L 29/0696 |
| 9,299,790 | B2 * | 3/2016 | Masuda | H01L 29/78 |
| 9,348,036 | B2 * | 5/2016 | Yamakawa | G01T 1/24 |
| 9,484,472 | B2 * | 11/2016 | Kasai | H01L 31/02005 |
| 9,530,902 | B2 * | 12/2016 | Kostamo | H01L 31/02005 |
| 9,547,089 | B2 * | 1/2017 | Elin | H01L 31/0352 |
| 9,613,992 | B2 * | 4/2017 | Shahan | G01T 1/243 |
| 9,847,369 | B2 * | 12/2017 | El-Hanany | H01L 27/14696 |
| 9,935,231 | B2 * | 4/2018 | Roehrer | H01L 27/1443 |
| 10,074,685 | B1 * | 9/2018 | Bakowski Holtryd | H01L 27/14658 |
| 10,120,082 | B2 * | 11/2018 | Ergler | A61B 6/4241 |
| 10,126,437 | B1 | 11/2018 | Danielsson | G01T 1/241 |
| 10,156,645 | B2 * | 12/2018 | Shahar | G01T 1/246 |
| 10,211,284 | B2 * | 2/2019 | Masuda | H01L 29/78 |
| 10,267,928 | B2 * | 4/2019 | Steadman Booker | G01T 1/244 |
| 10,448,914 | B2 * | 10/2019 | Spahn | H04N 5/335 |

* cited by examiner

X-RAY SENSOR, METHOD FOR CONSTRUCTING AN X-RAY SENSOR AND AN X-RAY IMAGING SYSTEM COMPRISING SUCH AN X-RAY SENSOR

TECHNICAL FIELD

The proposed technology generally relates to X-ray applications such as X-ray imaging, and more particularly to an X-ray sensor, also referred to as an X-ray detector. The proposed technology also relates to a method for constructing an X-ray sensor and an X-ray imaging system having a detector system that comprises such an X-ray sensor.

BACKGROUND

Radiographic imaging such as X-ray imaging has been used for years in medical applications and for non-destructive testing.

Normally, an X-ray imaging system includes an X-ray source and an X-ray detector system. The X-ray source emits X-rays, which pass through a subject or object to be imaged and are then registered by the X-ray detector system. Since some materials absorb a larger fraction of the X-rays than others, an image is formed of the subject or object. The X-ray detector may be of different types, including energy-integrating detectors and photon-counting detectors.

A traditional X-ray detector design normally includes, on the top side, an active detector area covered by detector diodes pixels, e.g. in the form of strips or rectangular or hexagonal areas p-type doped in the case the substrate is an n-type high resistivity material. The top side also includes a so-called junction termination area including a so-called guard.

For maximum sensitivity the highly resistive n-type part of the detector that builds a so called drift region of the PiN diode structure must be totally depleted of charge. This requires applying a voltage of at least 400 Volts for a 500-550 μm thick n-type region without reaching a condition of junction breakdown at the position of the maximum electric field in the structure. Furthermore, the detector must sustain significantly higher voltage to secure tolerance to the positive surface charge which is created as a result of irradiation in the passivating oxide. This is known to increase the electric field at the surface and reduce the breakdown voltage. The function of the junction termination is to spread the electric field along the surface of the detector in order to reduce the electric field strength and to secure the tolerance to the positive oxide charge and long enough lifetime of the detector under irradiation.

There are two main concepts of the junction termination that are applied to PiN diodes and detectors. One is Multiple Floating Field Rings MFFR and the second is so called Junction Termination Extension JTE. The MFFR uses the principle of dividing the applied reverse voltage into small fractions contained in the spaces between floating rings surrounding the anode p+ pixels covered area and the JTE uses the principle of charge neutrality between the dopant charge in the JTE under depletion negatively charged acceptors and in the n-type drift region also under depletion positively charged donors. A characteristic of both techniques is that they use a large area. The very principle of the field reduction is to widen the depletion region width at the surface as compared to that in the bulk of the material. For the required voltages of 400V to 800V the width of the junction termination is between 100 μm and 500 μm including the guard. The floating rings are normally equipped with metal plates helping to avoid the potential crowding at the edges of the pixel diodes.

The guard is the outermost electrode contacting the outermost p-type doped ring with a function to collect the leakage current from the areas outside of the detector and towards the detector edge. This electrode is normally connected to the ground.

A particular drawback of the termination is the loss of the active detector area. Also, since many detectors are combined to cover larger area the lost area in each individual detector constitutes "dead" or blind areas in the detector matrix which has a negative influence on the quality of the obtained image.

U.S. Pat. No. 4,377,816 relates to a semiconductor element having at least one p-n junction and provided with zone guard rings for improving the suppression behavior of the p-n junction. The zone guard ring substantially acts as a so called channel stopper field stop to prevent the space charge region electric field from reaching the edge of the device and thus prevent leakage of current. This represents a simple planar diode without any junction termination and with the only protection of preventing the electric filed from reaching the side wall surface of the device.

U.S. Pat. No. 8,093,624 relates to an avalanche photodiode having a device structure that enables a fill-factor approaching 100% at visible and near-infrared wavelengths, eliminating the need for optical focusing techniques. There is provided an n-type active region and a p-type active region. A first one of the n-type and p-type active regions is disposed in a semiconductor substrate at a first substrate surface. A second one of the n-type and p-type active regions includes a high-field zone disposed beneath the first one of the active regions at a first depth in the substrate, a mid-field zone disposed laterally outward of the first active region at a second depth in the substrate greater than the first depth, and a step zone connecting the high-field zone and the mid-field zone in the substrate. With this configuration, the photodiode structure prevents non-avalanche photoelectron collection by substantially inhibiting photoelectron paths that circumvent the high-field avalanche region of the device. Conventional channel stop regions, provided as p+ regions, are located at the edges of the photodiode. The photodiode may also include a conventional guard ring structure at the periphery of the cathode, laterally surrounding the photodiode cathode, e.g., in a circular configuration. The avalanche photodiode operates at avalanche condition breakdown at low voltage, and the issue of terminating the entire array of pixel diodes is not addressed. U.S. Pat. No. 8,093,624 rather concerns the design and configuration of individual photodiodes, where channel stoppers are used to separate individual pixel diodes.

EP 0661753 A1 relates to an improved edge termination scheme for semiconductor structures including field-limiting rings having a fine-to-coarse incrementing scheme which is spatially additive assuring constancy against lateral junction variation. This spatially increasing scheme greatly enhances breakdown voltage characteristics. Additionally, redundant rings are used to further guarantee insensitivity of the device to manufacturing variations.

Despite all the efforts invested in the design of detectors there is still room for improvement. The proposed technology aims to provide an X-ray detector with improved junction termination, in particular a junction termination that utilizes floating field limiting rings.

SUMMARY

In general, it is an object to provide an improved X-ray sensor, sometimes also referred to as an X-ray detector, having a junction termination that comprises Floating Field Limiting Rings. Such Floating Field Limiting Rings, FFRs, are sometimes referred to as Field Limiting Rings, FLRs.

It is a particular object to provide an improved X-ray sensor where the FLRs are spatially distributed in such a way that one obtain a more uniform surface electric field distribution.

In particular, it is desirable to provide an X-ray sensor where the electrical field peaks over the junction termination have well balanced magnitudes over all the FLRs. A uniform surface electric field distribution enables a junction termination that occupies a reduced amount of space and thus reduces the non-active area.

It is also an object to provide a method for constructing an X-ray sensor having the above mentioned features.

Another object is to provide an X-ray imaging system comprising such an X-ray sensor.

These and other objects are met by embodiments of the present invention.

According to a first aspect there is provided an X-ray sensor having an active detector region comprising a plurality of detector diodes arranged on a surface region of the X-ray sensor the X-ray sensor further comprising a junction termination surrounding the surface area comprising the plurality of detector diodes, the junction termination comprising a guard (5) arranged closest to the end of the surface region, a field stop arranged outside the guard and a number N of field limiting rings, FLRs arranged between the guard and the field stop, wherein each of the FLRs (7) are positioned so that the distance between the guard and the first FLR and the distances between different FLRs fulfills the following constraints:
  the distances lie within an effective area, the effective area being bounded by the lines $\alpha=(10+1.3\times(n-1))$ μm and $\beta=(5+1.05\times(n-1))$ μm, and
  the distance between successive FLRs (7) is either constant or increases with increasing n where n denotes the index of the FLRs (7), wherein $1 \leq n \leq N$.

According to a second aspect there is provided a method for constructing an X-ray sensor. The method comprises providing a plurality of detector diodes on a surface region of a material substrate. The method also comprises providing (S2) the material substrate with a junction termination surrounding the surface region; wherein the junction termination is constructed by:
  providing a guard ring adjacent the surface region, and
  providing a field stop outside of the guard ring, and
  selecting a number N of positions, the positions being selected so that distances between different FLRs and the distance between the guard and the first FLR_fulfills the following constraints:
  the distances lie within an effective area bounded by the lines $\alpha=(10+1.3\times(n-1))$ μm and $\beta=(5+1.05\times(n-1))$ μm, and
  the distance between successive FLRs (7) increases, or is the same, with increasing n where n denotes the index of the positions and $1 \leq n \leq N$.

The method also comprises placing a field limiting ring, FLR, at each of the selected positions.

According to a third aspect there is provided an X-ray imaging system. The X-ray imaging system comprises an X-ray source configured to emit X-rays. The X-ray imaging system also comprises an X-ray controller connected to the X-ray source and configured to control emission of X-rays from the X-ray source. The X-ray imaging system also comprises an X-ray detector system that comprises at least one X-ray detector according to the first aspect.

The basic idea of the proposed technology is to provide an X-ray sensor where Field Floating Rings, FFRs, are given a spatial distribution that ensures that the magnitude of electrical field peaks are well balanced over all the rings. Such balanced electrical field peaks will reduce the risks that the sensor will be damaged by high voltages, i.e., voltages exceeding the break through voltage of the sensor material and will at the same time enable a better use of the area occupied by the termination.

Other advantages will be appreciated when reading the detailed description.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Figure 1:
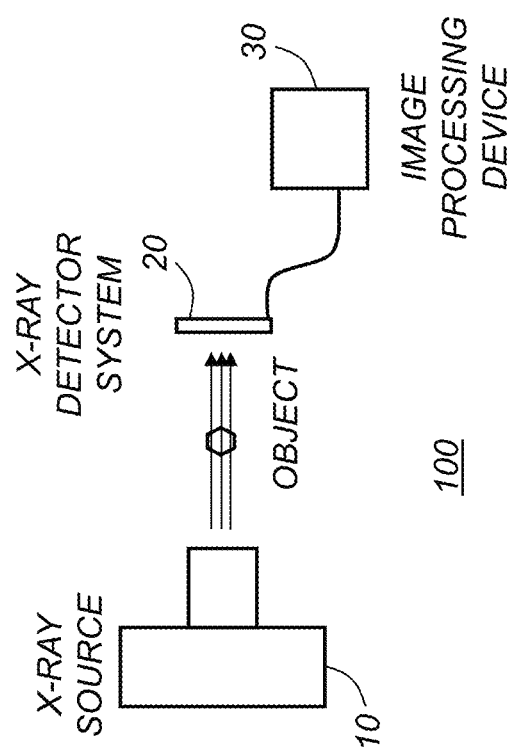
FIG. 1 is a schematic diagram illustrating an example of an overall X-ray imaging system.

It may be useful to begin with a brief overview of an illustrative overall X-ray imaging system, with reference to FIG. 1. In this non-limiting example, the X-ray imaging system 100 basically comprises an X-ray source 10, an X-ray detector system 20 and an associated image processing device 30. In general, the X-ray detector system 20 is configured for registering radiation from the X-ray source 10 that may have been focused by optional X-ray optics and passed an object or subject or part thereof. The X-ray detector system 20 is connectable to the image processing device 30 via suitable analog processing and read-out electronics which may be integrated in the X-ray detector system 20 to enable image processing and/or image reconstruction by the image processing device 30.

Figure 2:
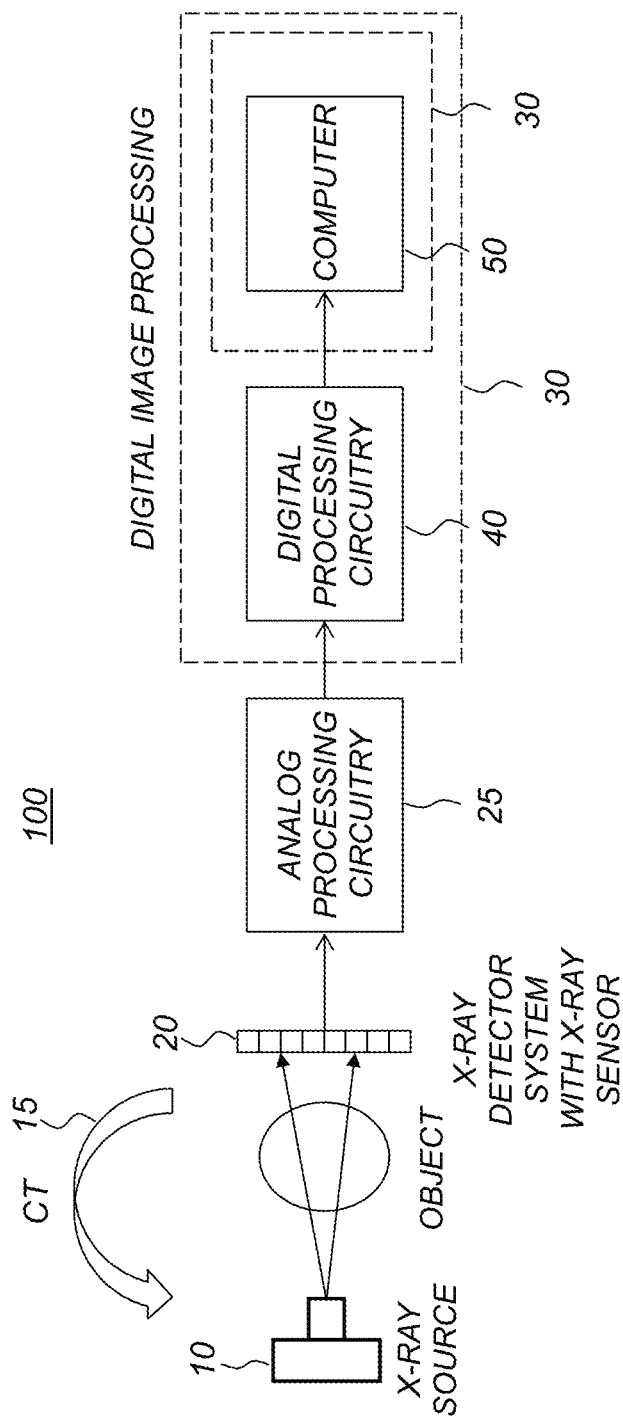
FIG. 2 is a schematic diagram illustrating another example of an X-ray imaging system.

As illustrated in FIG. 2, another example of an X-ray imaging system 100 comprises an X-ray source 10, which emits X-rays; an X-ray detector system 20, which detects the X-rays after they have passed through the object; analog processing circuitry 25, which processes the raw electrical signal from the detector and digitizes it; digital processing circuitry 40 which may carry out further processing operations on the measured data such as applying corrections, storing it temporarily, or filtering; and a computer 50 which stores the processed data and may perform further post-processing and/or image reconstruction.

The overall detector may be regarded as the X-ray detector system 20, or the X-ray detector system 20 combined with the associated analog processing circuitry 25.

The digital part including the digital processing circuitry 40 and/or the computer 50 may be regarded as a digital image processing system 30, which performs image reconstruction based on the image data from the X-ray detector system 20. The digital image processing system 30 may thus be seen as the computer 50, or alternatively the combined system of the digital processing circuitry 40 and the computer 50, or possibly the digital processing circuitry 40 by itself if the digital processing circuitry 40 is further specialized also for image processing and/or reconstruction.

An example of a commonly used X-ray imaging system 100 is a Computed Tomography CT system, which may include an X-ray source 10 that produces a fan or cone beam of X-rays and an opposing X-ray detector system 20 for registering the fraction of X-rays that are transmitted through a patient or object. The X-ray source 10 and the X-ray detector system 20 are normally mounted in a gantry 15 that rotates around the imaged object.

Accordingly, the X-ray source 10 and the X-ray detector system 20 illustrated in FIG. 2 may thus be arranged as part of a CT system, e.g. mountable in a CT gantry 15.

Modern X-ray detectors normally need to convert the incident X-rays into electrons, this typically takes place through photo absorption or through Compton interaction and the resulting electrons are usually creating secondary visible light until its energy is lost and this light is in turn detected by a photo-sensitive material. There are also detectors, which are based on semiconductors and in this case the electrons created by the X-ray are creating electric charge in terms of electron-hole pairs which are collected through an applied electric field.

Conventional X-ray detectors are energy integrating, the contribution from each detected photon to the detected signal is therefore proportional to its energy, and in conventional CT, measurements are acquired for a single energy distribution. The images produced by a conventional CT system therefore have a certain look, where different tissues and materials show typical values in certain ranges.

Photon counting detectors have also emerged as a feasible alternative in some applications; currently those detectors are commercially available mainly in mammography. The photon counting detectors have an advantage since in principle the energy for each X-ray can be measured which yields additional information about the composition of the object. This information can be used to increase the image quality and/or to decrease the radiation dose.

Compared to the energy-integrating systems, photon-counting CT has the following advantages. Firstly, electronic noise that is integrated into the signal by the energy-integrating detectors can be rejected by setting the lowest energy threshold above the noise floor in the photon-counting detectors. Secondly, energy information can be extracted by the detector, which allows improving contrast-to-noise ratio by optimal energy weighting and which also allows so-called material basis decomposition, by which different materials and/or components in the examined subject or object can be identified and quantified, to be implemented effectively. Thirdly, more than two basis materials can be used which benefits decomposition techniques, such as K-edge imaging whereby distribution of contrast agents, e.g. iodine or gadolinium, are quantitatively determined. Fourth, there is no detector afterglow, meaning that high angular resolution can be obtained. Last but not least, higher spatial resolution can be achieved by using smaller pixel size.

The most promising materials for photon-counting X-ray detectors are cadmium telluride CdTe, cadmium zinc telluride CZT and silicon Si. CdTe and CZT are employed in several photon-counting spectral CT projects for the high absorption efficiency of high-energy X-rays used in clinical CT. However, these projects are slowly progressing due to several drawbacks of CdTe/CZT. CdTe/CZT have low charge carrier mobility, which causes severe pulse pileup at flux rates ten times lower than those encountered in clinical practice. One way to alleviate this problem is to decrease the pixel size, whereas it leads to increased spectrum distortion as a result of charge sharing and K-escape. Also, CdTe/CZT suffer from charge trapping, which would lead to polarization that causes a rapid drop of the output count rate when the photon flux reaches above a certain level.

In contrast, silicon has higher charge carrier mobility and is free from the problem of polarization. The mature manufacturing process and comparably low cost are also its advantages. But silicon has limitations that CdTe/CZT does not have. Silicon sensors must accordingly be quite thick to compensate for its low stopping power. Typically, a silicon sensor needs a thickness of several centimeters to absorb most of the incident photons, whereas CdTe/CZT needs only several millimeters. On the other hand, the long attenuation path of silicon also makes it possible to divide the detector into different depth segments, as will be explained below. This in turn makes it possible for a silicon-based photon-counting detector to properly handle the high fluxes in CT.

When using simple semiconductor materials, such as silicon or germanium, Compton scattering causes many X-ray photons to convert from a high energy to a low energy before conversion to electron-hole pairs in the detector. This results in a large fraction of the X-ray photons, originally at a higher energy, producing much less electron-hole pairs than expected, which in turn results in a substantial part of the photon flux appearing at the low end of the energy distribution. In order to detect as many of the X-ray photons as possible, it is therefore necessary to detect as low energies as possible.

A traditional X-ray sensor/detector design normally includes, on the top side, an active detector area covered by detector diode pixels, e.g. in the form of strips or rectangular or hexagonal areas p-type doped in the case the substrate is an n-type high resistivity material. According to the predominant trend in X-ray sensor/detector design, the top side also includes a so-called junction termination area. The proposed technology aims to provide an X-ray detector having an improved junction termination. The inventors have in particular realized that a specific distribution of FLRs yield electrical field peaks that are highly balanced over the FLRs. That is, the magnitude of the electrical field peaks are nearly the same over the FLRs. This follows from the particular distribution of the FLRs relative the guard ring of the junction termination. Before describing the features of the proposed X-ray sensor there will be provided a brief description of an X-ray sensor provided with FLRs. It should be noted FLRs are sometimes referred to as floating rings or even floating field limiting rings, FLR.

Figure 3:
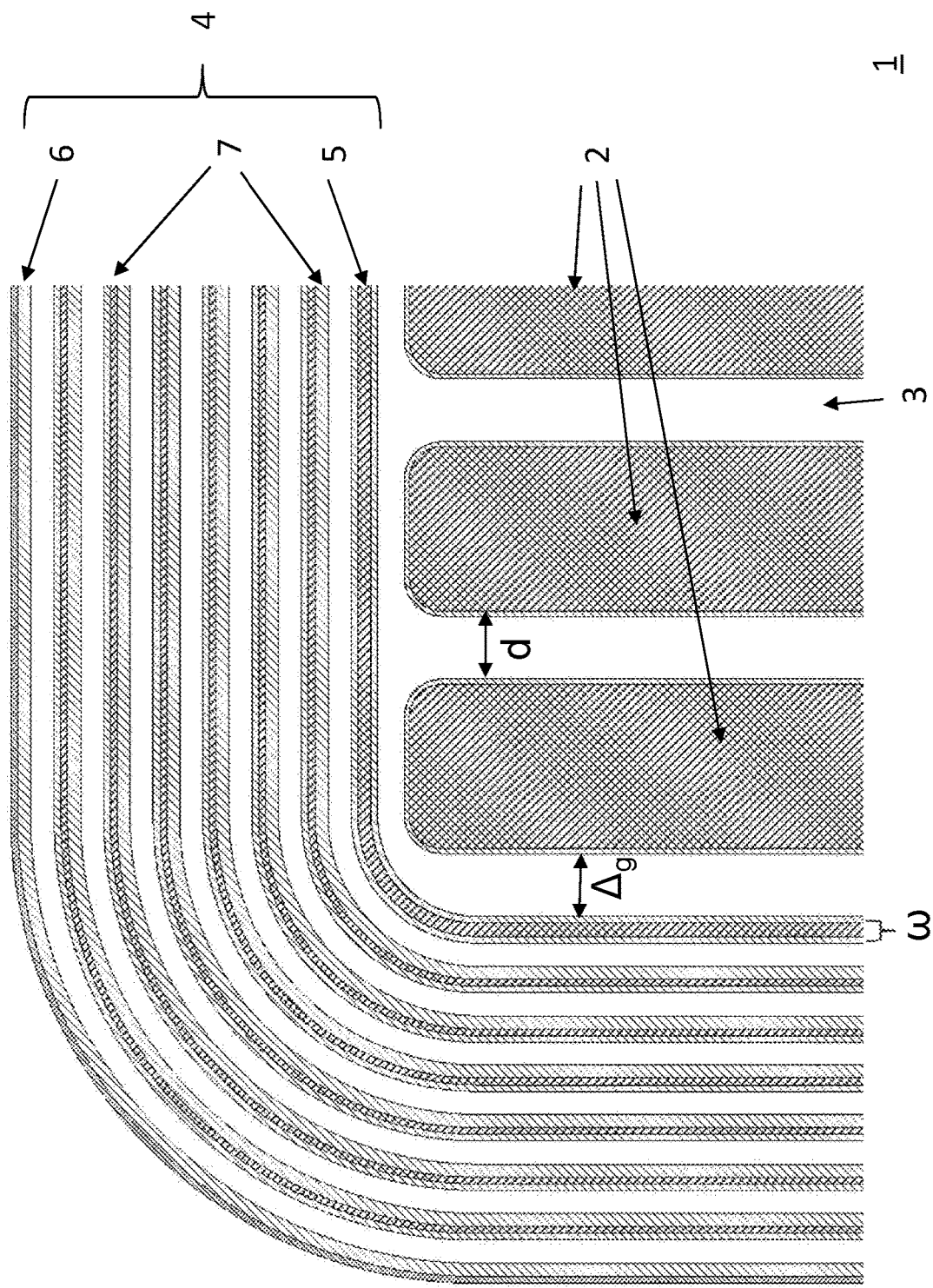
FIG. 3 is a schematic diagram illustrating an example of an X-ray sensor seen from a top view according to an embodiment.

In order to describe a sensor design utilizing FLRs, reference is made to FIG. 3. In FIG. 3 it is illustrated how a number of diodes 2, e.g., pixel diodes, are enclosed by a junction termination comprising a guard 5, sometimes referred to as a guard ring, a field stop 6 and a number of FLRs 7 arranged between the guard 5 and the field stop 6. In the sensor design depicted in FIG. 3 the function of the guard 5 and that of FLRs 7 are typically distinctly different and separated. The function of the FLRs 7 is to control the electric field at the sensor periphery and at the surface of the sensor.

Normally, the function of the guard 5 is entirely to collect the leakage current generated at the periphery of the sensor being an array of pixel diodes 2. The FLR concept may be used to terminate high voltage planar p-n junctions and is based on the positioning of a number of diffused concentric rings of the same doping type as that of the highly doped side of the diode that surrounds the p-n junction. The electric potential is taken up by the spaces between the diffused rings upon the application of the reverse voltage to the diode. The diffused rings are often equipped with field plates in metal or polysilicon to spread and soften the electric field distribution close to the edges of the in-diffused p-n junctions created on both sides of the diffused rings. Usually a large number of equidistant rings is required in order to keep the potential between the rings, and thus the surface electric field, low enough with respect to the passivating materials. The number of rings increases with the value of the blocking voltage and FLR termination is normally not space efficient since it requires a relatively large surface area. In addition to the FLR structure a field stop ring is often provided outside of the rings by using dopant of opposite type to the rings in order to prevent an expansion of the space charge region towards the defective edge area of the chip. The significance of the n-stop ring is only limited to the case of the surface charge of opposite polarity which means negative charge in the case of the n-type low doped detector bulk material and p-type anode region and p-type FLR rings. Normally positive surface charge is expected as a result of the X-ray exposure at the oxidized silicon surface.

A particular objective of the proposed FLR design, to be used for X-ray detectors, is to reduce the lateral extension of the termination in order to reduce the loss of active sensor area while at the same time ensuring that there is a balance among the electrical field peaks over the various FLRs. That is, that the magnitude of the electrical field peaks are comparatively the same over different FLRs.

The most space efficient termination is the one that results in a rectangular distribution of the surface electric field. This follows from the Poisson equation according to which blocking voltage is an integral of the electric field. In the case of the FLR termination the electric field distribution at the surface consists of a sum of triangular distributions from each of the spaces between the rings. In order to reduce the lateral expansion of the termination the spacing between the rings must be dimensioned in such a way as to secure equal electric field peak height in all the spacing and also to minimize the width of the diffused rings.

Furthermore, from the point of view of reliability, the quasi-uniform, equal field peaks distribution has to be maintained during the predicted life of the sensor. Under exposure to X-ray irradiation the build-up of positive surface charge takes place in the oxide close to the silicon and silicon dioxide interface. The positive surface charge causes shift of the electric field distribution towards the p-n junction periphery in the case of the highly doped side of the junction being p-type. This means that the electric field maxima belonging to the innermost rings increase and those of the outer rings decrease. The electric field distribution becomes skewed with maximum shifted towards the main p-n junction, i.e., the outer edge of the p-n junction belonging to the guard ring. The space efficient design must be geared in such way as to equalize the electric field maxima in full extension of the termination in the wide range of surface charge values or at least from 0 to $1 \times 10^{12}$ cm$^{-2}$.

Based on this the proposed technology provides mechanisms whereby at least three complications are addressed. The proposed FLR distribution ensures a reduced lateral extension of the FFR junction termination. This in turn ensures a larger active detection area. The proposed FLR distribution also ensures a uniform surface electric field distribution. This means, in the case of FFR termination, a comparatively equal magnitude of the electric field peaks. The proposed FLR distribution also ensures a reduced sensitivity to the positive surface charge. This follows from the fact that the electric field distribution will be uniform up to the highest possible values of the concentration of positive surface charge. X-ray detectors are naturally exposed to X-ray radiation. It is known that X-ray radiation causes accumulation of the positive charge in the oxide covering the surface of the detector. The positive surface charge causes shift of the electric field distribution towards the guard and an increase of the electric field value between the guard and the first ring in the FFR termination. This causes an increase of the leakage current and finally a loss of the voltage blocking properties, i.e., a reduction of the maximum blocking voltage. This is part of the aging of the detector and constitutes an important feature impacting the lifetime of the detector in the application.

Figure 8:
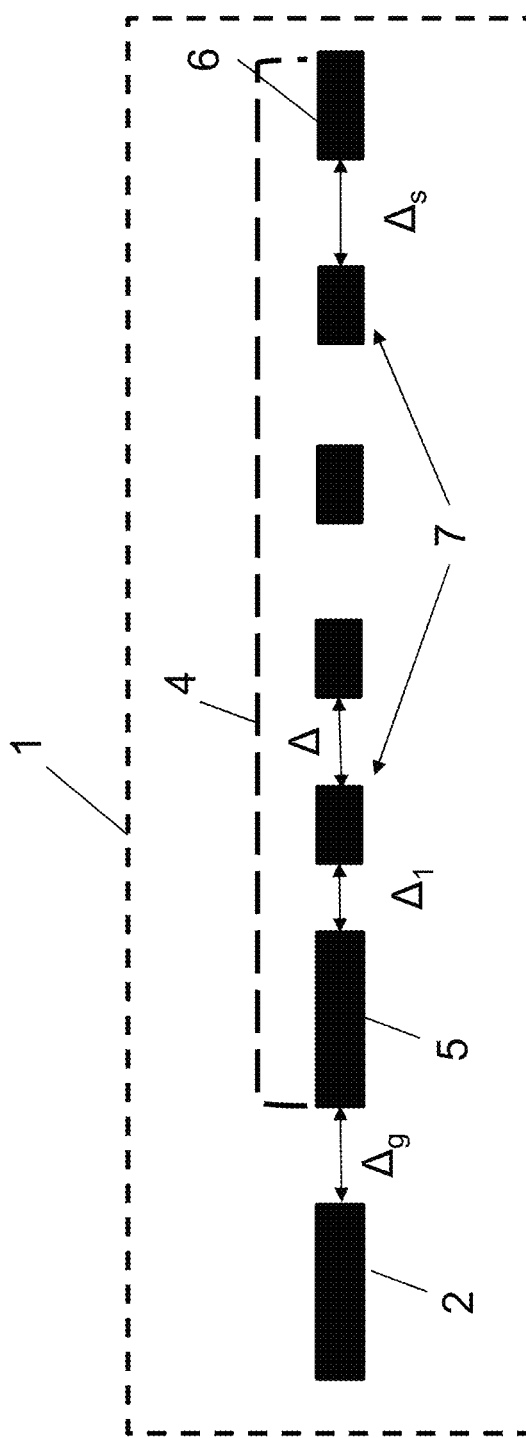
FIG. 8 is a schematic cross-sectional illustration of part of an X-ray sensor comprising a junction termination having FLRs.

Reference is now made to FIG. 8 which illustrates a cross-section of an X-ray sensor comprising a junction termination according to the sensor design depicted in FIG. 3. Here the schematically illustrated X-ray sensor 1 comprises detector diodes 2, a junction termination 4 and a field stop 6. The junction termination comprises in turn a guard 5 and a number of FLRs 7. The distances Δ between neighboring FLRs are constant in this configuration, i.e., it is the same distance Δ between each pair of neighboring FLRs. The drawing also illustrates three additional distances, a distance $\Delta_g$ between the guard ring 5 and the closest detector element 2, a distance $\Delta_1$ between the guard 5 and the first FLR 7, and a distance $\Delta_S$ between the last FLR and the field stop 6. It should be noted that the doping of the FLRs are opposite to the doping of the detector material. That is, if the detector material, e.g., silicon, is of n-type, then the doping of the FLRs are of p-type.

Before proceeding we provide a short description of the notation used in the present disclosure. With the notation $X_n$ is in what follows intended a distance from the center of a FLR to the outer edge of the guard. With the center of a FLR is intended the center or midpoint of the FLR with regard to the width dimension. If a FLR has a width a the center point of the FLR is located at σ/2. With the outer edge of guard is intended the edge of the guard that is closest to the FLRs. That is, the guard faces, on its inner side, the detector diodes 2, and on its opposing edge the guard faces the FLRs. The opposing edge is thus referred to as the outer edge. The notation $\Delta_n$ specifies the separation distance between neighboring FLRs or between the guard ring and its closest FLR, $\Delta_1$ may for example denote the separation distance between the guard and the first FLR, that is, the FLR that is provided closest to the guard. $\Delta_2$ may in the same manner denote the separation distance between the first FLR and the second FLR, etc. It should be noted that the separation distances refer to the distance between the edges of the FLRs that are facing each other. If the width of the FLRs are taken into consideration the distance between the center point of the first FLR and the center point of the second FLR will be given by $\Delta_2+\sigma$, where σ is the width of a FLR.

Figure 9:
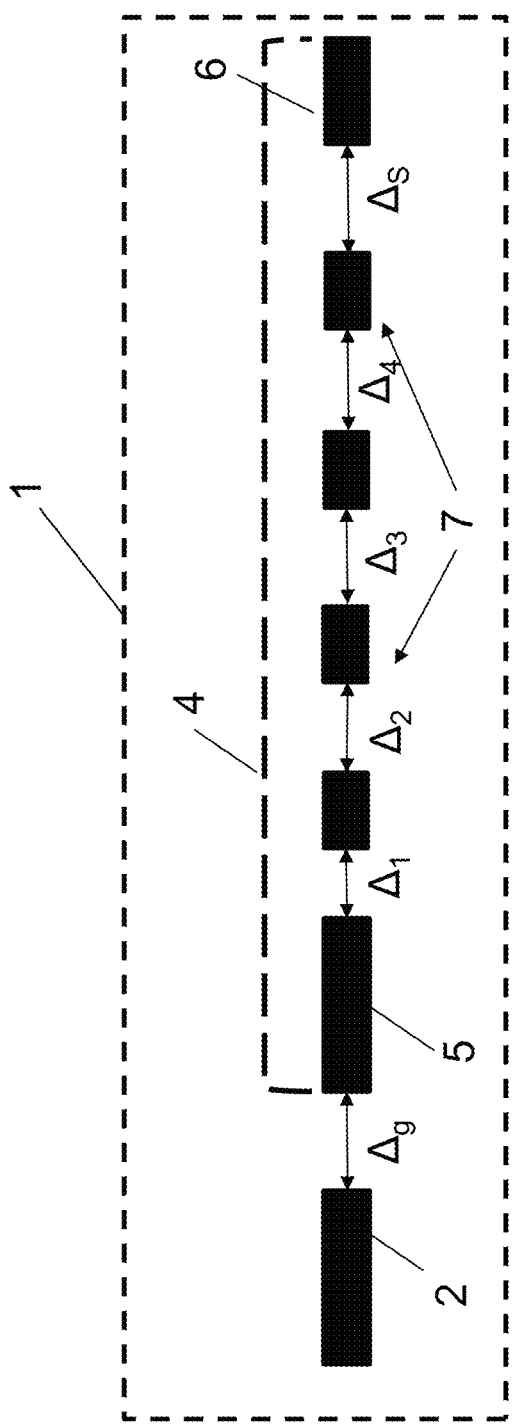
FIG. 9 is a schematic cross-sectional illustration of part of an X-ray sensor comprising a junction termination having FLRs. The individual distances between neighboring FLRs are shown.

The proposed technology aims to improve upon the design illustrated in FIG. 8. It aims in particular to provide a specific design of the junction termination where individual FLRs are positioned in a particular way, i.e., where the distances between neighboring FLRs are selected to fulfill specific criteria. With reference to FIG. 9, which illustrates the same cross-section as FIG. 8, the proposed technology provides an X-ray sensor where the specific distances $\Delta_n$ between adjacent FLRs are selected to achieve a particularly effective junction termination. For the design in FIG. 9, which comprises four FLRs, this corresponds to selecting four distances, $\Delta_1$, $\Delta_2$, $\Delta_3$ and $\Delta_4$, and optionally also the distance $\Delta_g$ between the guard ring and the closest detector diode 2 and the distance $\Delta_S$ between the last FLR and the field stop 6. A special limitation also applies to the distance $\Delta_g$ between the inner edge of the guard and outer edge of the sensor pixel or detector diodes closest to the guard. This distance should, according to the proposed technology, preferably be selected from the interval 10 μm≤$\Delta_g$≤100 μm, and even more preferably from the interval 20 μm≤$\Delta_g$≤40 μm.

Figure 4:
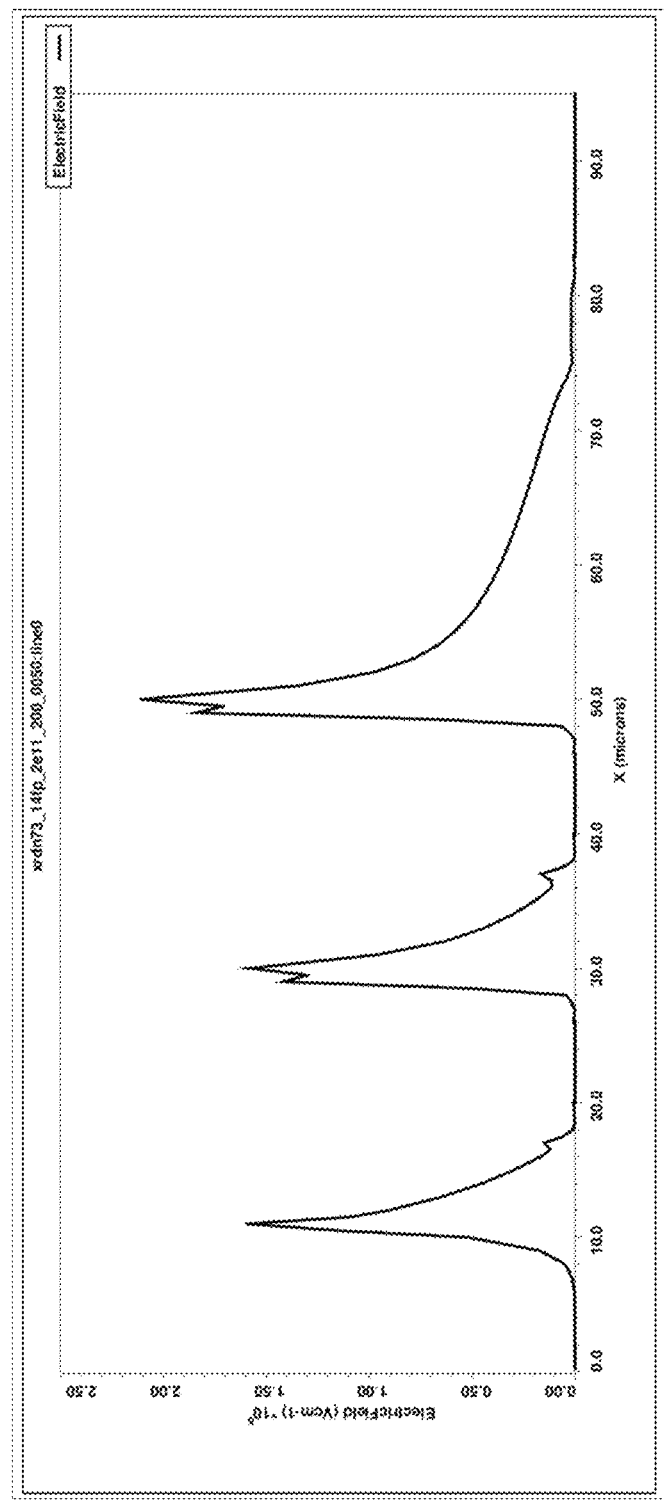
FIG. 4 is a graph illustrating a well-balanced electric field peak profile when three Field Limiting Rings, FLRs, are used in the junction termination.

Before describing particular embodiments of the proposed technology there will be provided a more general description of the cooperating features underlying the sensor. The inventors have realized that a particularly important characteristic for a sensor with a junction termination using FLRs is to obtain a balanced field peak profile over all the FLRs. That is, the electric field peaks should preferably have the comparatively same magnitude over all FLRs. To highlight this insight reference is made to FIG. 7 which illustrates the electric field peaks of a particular junction termination that utilizes a relatively large number of equidistantly placed FLRs. As is clear from the graph there is a large difference in field peak magnitudes over the various FLRs. What is wanted is instead more of a profile as shown in e.g., FIGS. 4, 5 and 6.

The inventors have also realized that in order to increase the active detector area the number N of FLRs should preferably be rather small, e.g., N≤10. To achieve the above mentioned balanced electric field peak profile while at the same time enabling the use of a small number of FLRs, a particular type of FLR-distance distribution is needed. The proposed technology aims to provide such a FLR-distance distribution.

The proposed FLR-distance distribution relates in fact to a whole family of FLR-distance distributions that are constrained to lie within a particular area, referred to as an effective area. To appreciate this concept reference is made to FIG. 11 which illustrates an area constrained by two lines. The y-axis in the graph refers to spacing values in micrometer, that is, the possible spacing's between two adjacent FLRs. The x-axis denotes the index of a particular spacing. The constraining lines illustrated by dashed lines have the functional form $\Delta_n=\Delta_1+\delta(n-1)$, where $\Delta_n$ denotes the distance between n:th FLR and the neighboring FLR that is closer to the guard 5, $\Delta_1$ denotes the distance between the guard 5 and the first FLR and δ denotes an increment in length between two neighboring FLRs. The inventors have realized that an effective area can be generated by selecting two different values for $\Delta_1$ and δ and generate two distinct lines using these values. The effective area is now defined as the area that lies between these generated lines. It has been found that if FLR-distance distributions are selected so that each distance separating a pair of neighboring FLRs is selected to lie in the effective area it will be possible to reduce the number of FLRs while still allowing a balanced electric field peak profile over all FLRs. To fully achieve this goal the FLR-distance distributions need to satisfy one additional constraint, namely that the distances $\Delta_n$ between neighboring FLRs needs to either grow with increasing n or be constant. With constant is here intended that at least a few pairs of neighboring FLRs may have the same distances between their respective FLRs. It may for example be that the distance between the fifth FLR and the sixth FLR is the same as the distance between the fourth and the fifth FLR.

Figure 10:
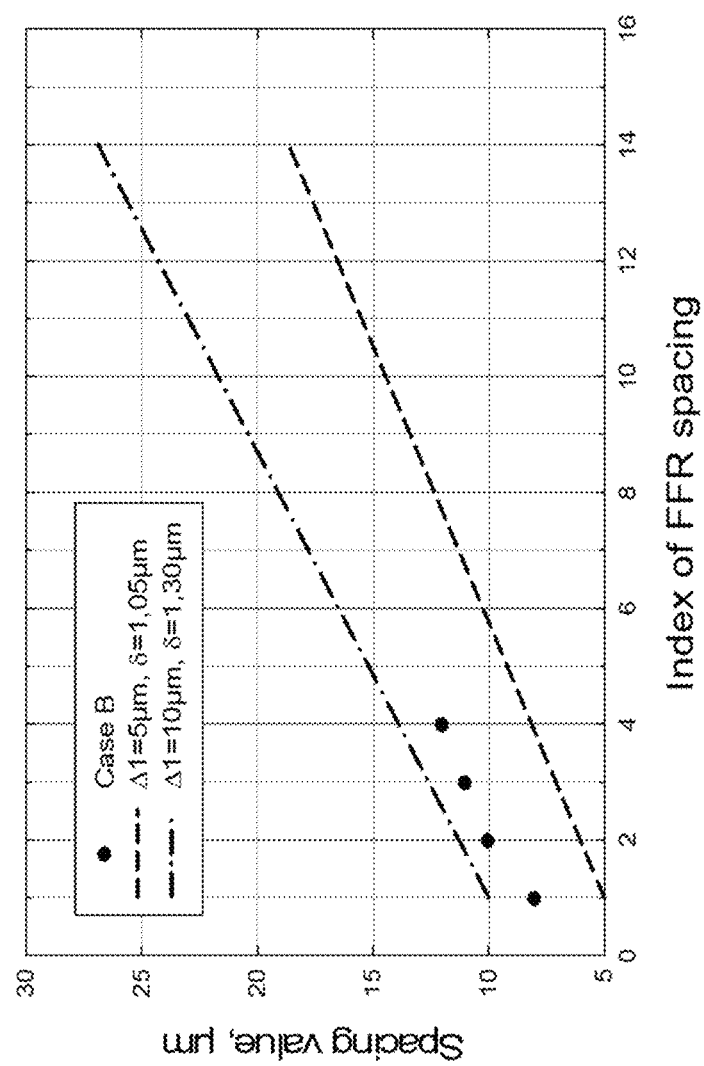
FIG. 10 is an exemplary graph illustrating the concept of an effective area. It is shown how specific distances between neighboring FLRs can be selected from points within the effective area. Here four distances are chosen, one distance between a FLR and the guard and three that corresponds to distances between neighboring FLRs.

As was mentioned above a FLR-distance distribution is to be selected so that each distance separating a pair of neighboring FLRs lie within the effective area that is partially enclosed by two different lines having the functional form $\Delta_n=\Delta_1+\delta(n-1)$. The first line α is generated by selecting $\Delta_1$=10 μm and δ=1.3 μm and the second line β is generated by selecting $\Delta_1$=5 μm and δ=1.05 μm. These lines are illustrated in FIG. 10. FIG. 10 illustrates a particular exemplary configuration showing how the distances separating the guard and four FLRs, illustrated by means of dots, are distributed. A first FLR is positioned so that it has a spacing of approximately 8 μm to the guard. A second FLR is positioned so that it has a spacing of approximately 10 μm to the first FLR. A third FLR is in turn positioned so that it has a spacing of approximately 11 μm to the second and a final fourth FLR is positioned so that it has a spacing of approximately 12 μm to the third FLR. As can be seen in the drawings the corresponding dots lie well within the effective area generated by the two lines and the distances between neighboring FLRs are increasing with increasing n.

Figure 11:
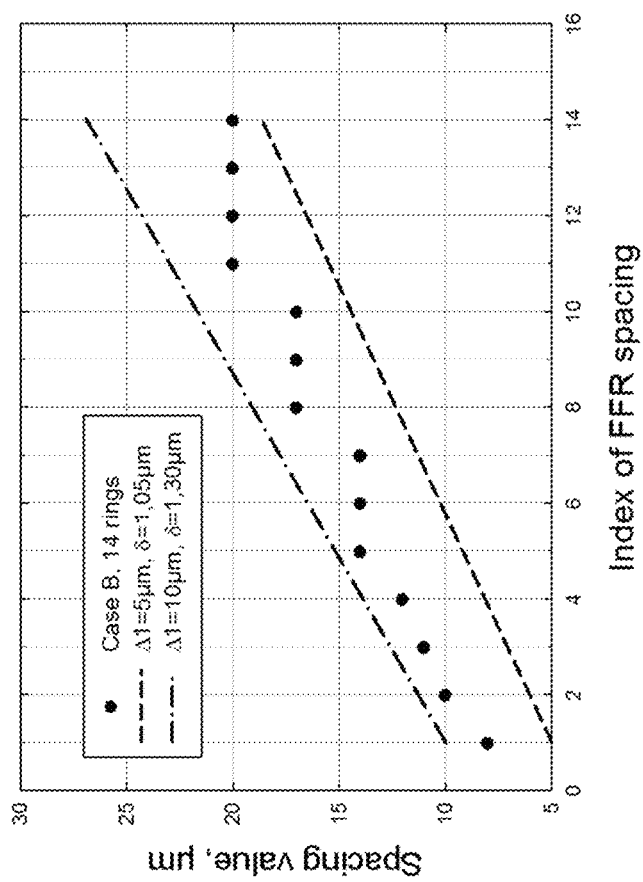
FIG. 11 is an exemplary graph illustrating the concept of an effective area. It is shown how specific distances between neighboring FLRs can be selected from points within the effective area. Here fourteen distances are chosen, one distance between a FLR and the guard and thirteen that corresponds to distances between neighboring FLRs.

Another particular example configuration is illustrated in FIG. 11. In this particular example 14 FLRs are to be distributed. To achieve this, 14 points in the effective area are to be chosen with the constraint that the distances between neighboring FLRs are increasing with increasing n or that at least some of them are constant over successive FLR pairs. The first four distances are chosen as in FIG. 10. The FLR with index 5 is provided at a distance of approximately 14 µm from the FLR with index 4. The FLRs with indices 6 and 7 are however given distances that are the same as the distance accorded to the FLR with index 5. That is, FLR with index 6 is provided at a distance approximately 14 µm from FLR with index 5 and FLR with index 7 is provided at a distance of approximately 14 µm from FLR with index 6. This is clearly illustrated in FIG. 11 as they all lie on the same horizontal line in the graph. FLR with index 8 is then positioned at a distance of approximately 17 µm from FLR with index 7, while FLRs with index 9 and 10 are given the same separation distances as FLR with index 8. Finally FLR with index 11 should be positioned at a distance of approximately 20 µm from FLR with index 10. FLRs with indexes 12, 13 and 14, are here provided with the same separation distance as FLR with index 11. It is clear from FIGS. 10 and 11 that all selected distances lie within the effective area and that all distances between successive FLRs 7 is either constant or increases with increasing n where n denotes the index of the FLRs 7, and $1 \leq n \leq N$, where N is the total number of FLRs. Even though the distances between the FLRs vary from 0 to 3 µm in this example, the average distance increment, as averaged over the whole distribution, is about 1.0 µm.

The provided examples illustrate the design rule underlying the proposed technology. At first an effective area is generated by two lines having the functional form $\Delta_n = \Delta_1 + \delta(n-1)$ with parameters as given above, i.e., a first line is generated by selecting $\Delta_1 = 10$ µm and $\delta = 1.3$ µm and a second line is generated by selecting $\Delta_1 = 5$ µm and $\delta = 1,05$ µm. After that particular separation distances are obtained by selecting points that lie within the area and that defines separation distances between neighboring FLRs that either grow with growing n or are constant and satisfy the condition that the δ value averaged over the entire separation distance distribution is contained within the interval from 1.05 to 1.3.

The proposed technology therefore provides an X-ray sensor 1 having an active detector region comprising a plurality of detector diodes 2 arranged on a surface region 3 of the X-ray sensor 1. The X-ray sensor 1 further comprising a junction termination 4 surrounding the surface area 3 comprising the plurality of detector diodes 2. The junction termination 4 comprising a guard 5 arranged closest to the end of the surface region 3, a field stop 6 arranged outside the guard 2 and a number N of field limiting rings, FLRs 7 arranged between the guard 5 and the field stop 6. Each of the FLRs 7 are positioned so that the distance between the guard 5 and the first FLR and the distances between different FLRs 7 fulfills the following constraints:

the distances lie within an effective area, the effective area being bounded by the lines $\alpha = (10+1.3 \times (n-1))$ µm and $\beta = (5+1.05 \times (n-1))$ µm, and the distance between successive FLRs 7 is either constant or increases with increasing n where n denotes the index of the FLRs 7, wherein $1 \leq n \leq N$.

To be more specific, the floating rings are constituted by in-diffused p-n junctions having a determined width and a specific metallization. Each of the FLRs are, according to the proposed technology, placed so that the distance between the outer edge of the p-n junction edge belonging to the preceding ring and the inner edge of the p-n junction of the following ring are selected to lie within an effective area bounded by two lines having the functional form $\Delta_n = \Delta_1 + \delta(n-1)$, where $\Delta_1$ denotes the distance between the outer edge of the guard p-n junction and the inner edge of the p-n junction of the first FLR, δ is a length increment and n is the index of the FLRs. The outer edge faces the direction of the sensor edge and the inner edge faces the direction of the proper sensor area. The two lines are $\alpha = 10+1.3 \times (n-1)$ µm and $\beta = 5+1.05 \times (n-1)$ µm. The FLRs are also placed so that the distance between successive FLRs is either constant or increases with increasing n where n denotes the index of the FLRs 30, and $1 \leq n \leq N$.

Figure 5:
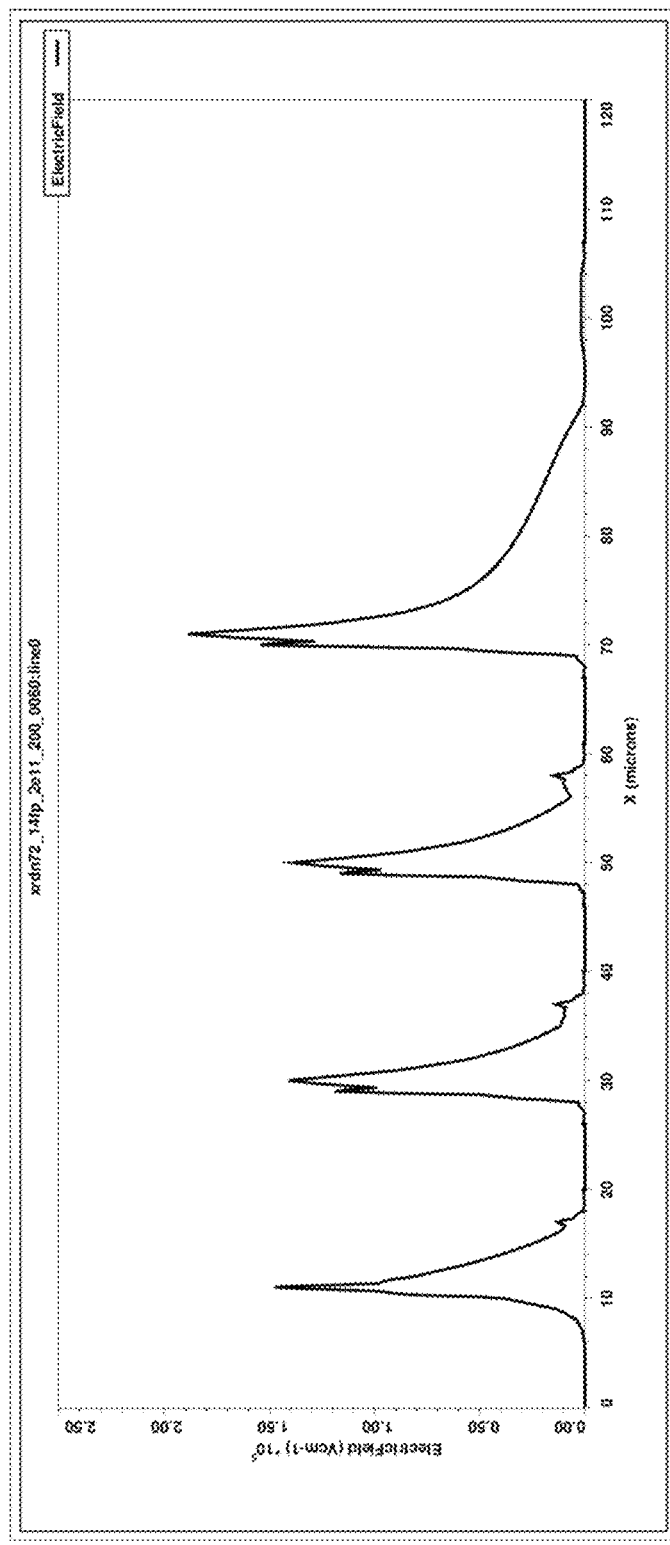
FIG. 5 is a graph illustrating a well-balanced electric field peak profile when four FLRs are used in the junction termination.
Figure 6:
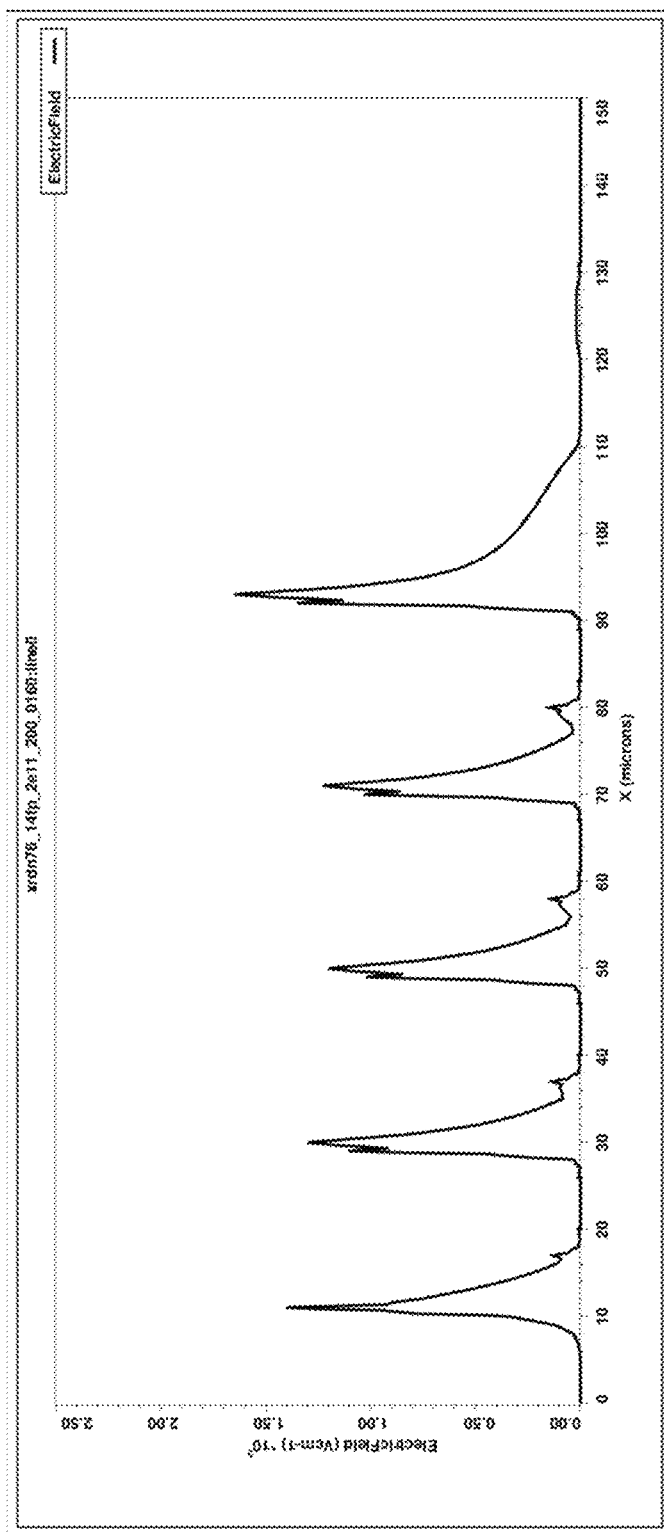
FIG. 6 is a graph illustrating a well-balanced electric field peak profile when five FLRs are used in the junction termination.
Figure 7:
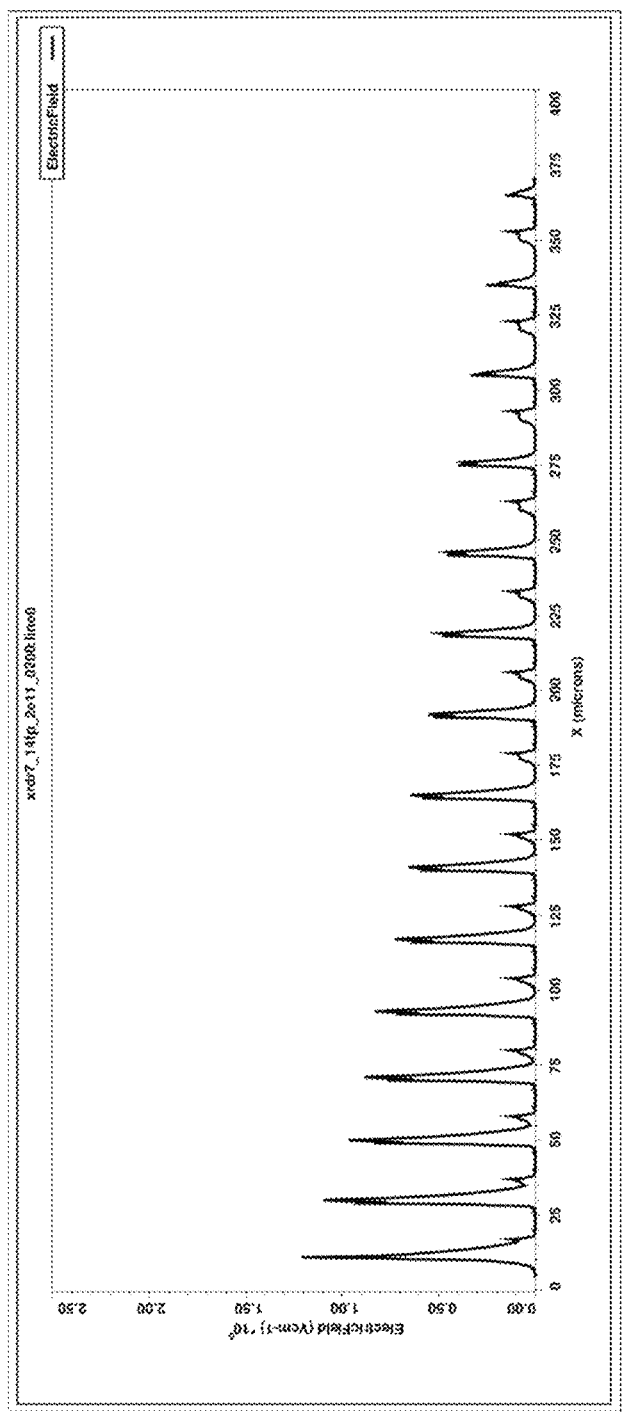
FIG. 7 is a graph illustrating an unbalanced electric field peak profile when a large number of FLRs are used.

The proposed technology provides an X-ray sensor wherein a number N of individual FLRs are positioned to ensure a balanced electric field peak profile as illustrated in e.g., FIGS. 5 and 6. The proposed technology has been shown to be especially effective when the number N of FLRs is relatively small, i.e., when the number N of FLRs is selected from the interval $1 \leq N \leq 10$.

Figure 13:
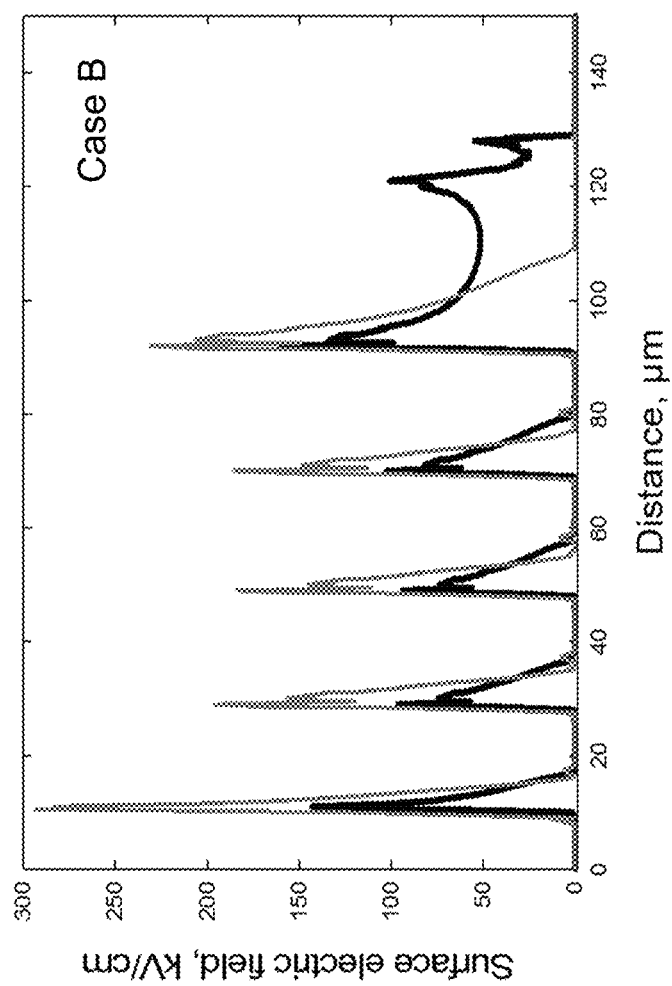
FIG. 13 is a graph illustrating a well-balanced electric field peak profile when five FLRs are used in the junction termination and where the positions of the FLRs has been selected according to the invention.
Figure 14:
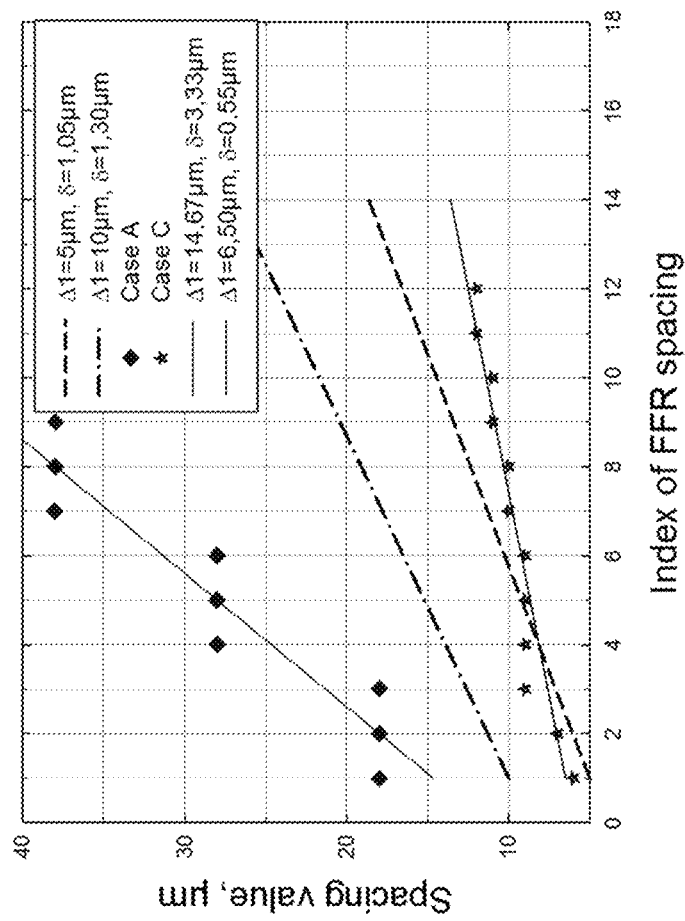
FIG. 14 is a graph illustrating how distances may be selected from areas in the graph that are not part of the effective area according to the invention. Two different cases, Case A and Case C are shown.
Figure 15:
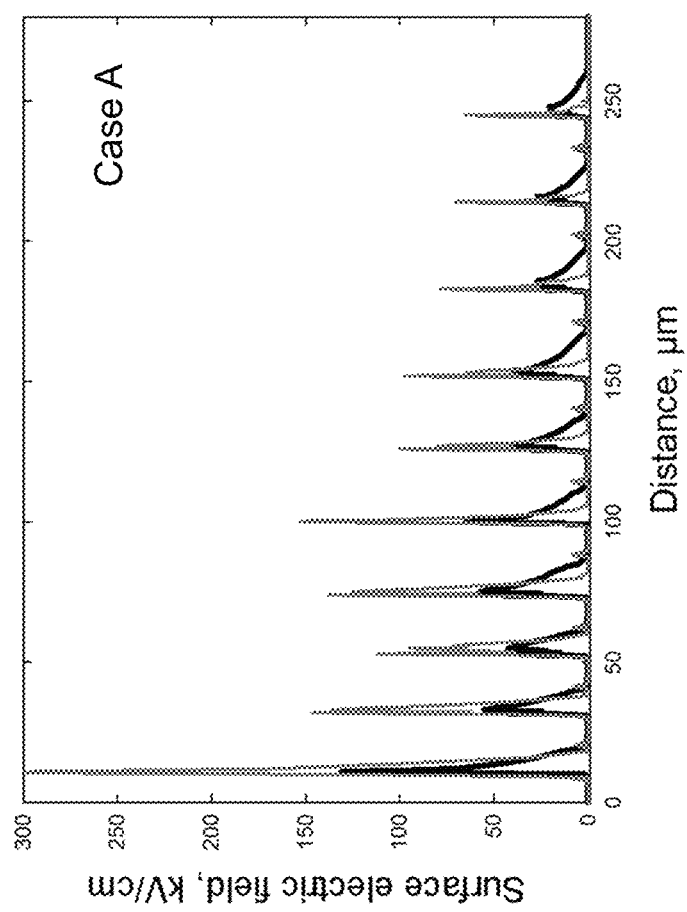
FIG. 15 is graph illustrating the unbalanced electric field peak profile one obtains when selecting positions according to Case A.
Figure 16:
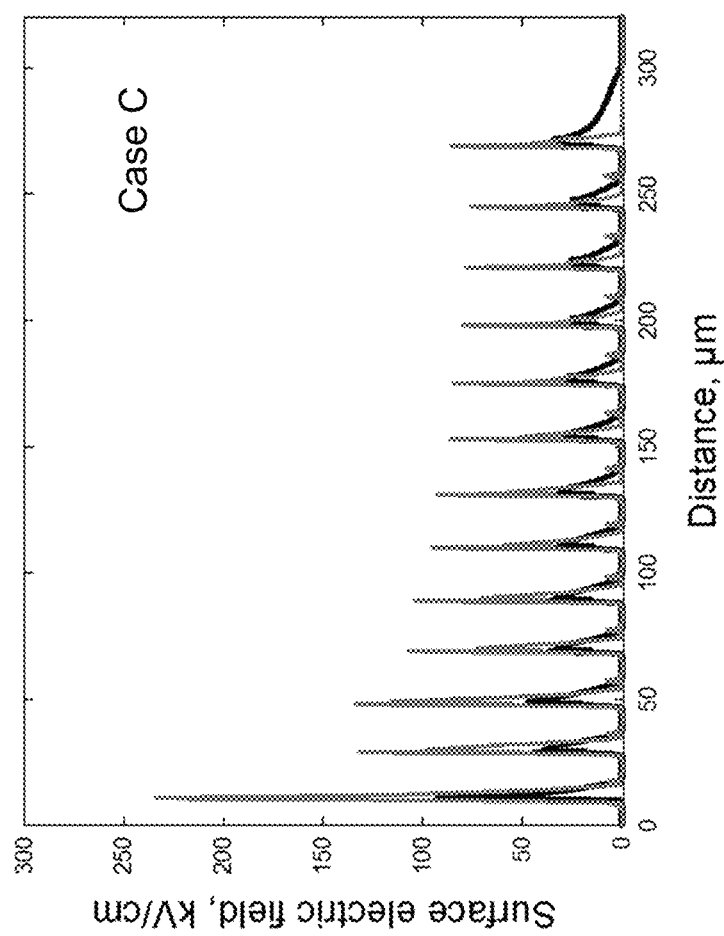
FIG. 16 is graph illustrating the unbalanced electric field peak profile one obtains when selecting positions according to Case C.

The electric field distribution for a particular illustrating configuration, denoted Case B, is provided in FIG. 13. The junction termination has 4 FLRs and the surface electric field distribution is shown for two values of positive surface charge at applied voltage of 500 V. This corresponds to the voltage required to deplete the whole volume of the 500 µm thick Shown is the surface electric field distribution for positive surface charge density of $1E10 \text{ cm}^{-2}$, the black line, and for positive surface charge density of $5E11 \text{ cm}^{-2}$, the gray line. A uniform electric field distribution is thereby obtained with reduced lateral extension of the junction termination even for high concentrations of the positive surface charge. This example can be contrasted with the graphs illustrated in FIGS. 15 and 16. These graphs corresponds to case A and case C, respecftully. Case A refers to a FLR configuration denoted by symbolic diamonds in FIG. 14, and Case C refers to a FLR configuration denoted by symbolic stars in FIG. 14. It is clear from FIGS. 15 and 16 that the profiles of the electric field peaks are in stark contrast to the field peaks obtained by means of the proposed technology.

All particular FLR-configurations may be selected with the proviso that they fulfill the criteria set out above. The configurations may be approximately linear configurations, as illustrated by FIG. 10 or non-linear configuration as schematically illustrated in FIG. 11. In what follows we will describe particular examples of more or less linear configurations. These configurations are obtained by selecting the distances between neighboring FLRs according to a distribution function of a particular linear form. The linear functional forms used to distribute the FLRs in these embodiments should all be selected so that distances between the neighboring FLRs lie within the specific effective area described earlier. The particular functional form that are to be used to distribute the FLRs is given by $\Delta_n = \Delta_1 + \delta(n-1)$. Note that the functional form coincide with the linear functional form that generates the effective area. This particular linear functional provides a way to generate distances between the FLRs, and consequently also individual positions for the FLRs given a determined width of the FLRs, if the distances between the FLRs are selected from the effective area specified as the area between the lines $\alpha = 10+1.3 \times (n-1)$ µm and $\beta = 5+1.05 \times (n-1)$ µm. The proposed technology thereby provides for a whole family of possible lines that can be used to generate the distances between the FLRs and the individual positions for the FLRs given a determined width of the FLRs.

Above it was described how individual distances between neighboring FLRs may be selected in order to obtain a junction termination with the desired features. The proposed technology also provides an alternative way to distribute the FLRs that achieves the same result. This alternative way, that also fulfills the earlier set criteria, i.e., distances fall within the effective area and distances are increasing or are constant with increasing n, distribute the FLRs relative the guard 5. That is, a number of positions $X_n$ are determined based on a certain FLR distributing function and the FLRs are placed at the determined positions. This alternative way may for example be used to distribute a number N of FLRs having a width dimension a relative the guard ring.

According to an embodiment of the proposed technology that takes into account the width dimension of a FLR, it is provided an X-ray sensor wherein a number n, where 1≤n≤N=total number of FLRs, of FLRs 7 are placed at a distance from the guard 5 given by the formula:

$$X_n = n\Delta_1 + \delta \Sigma_{i=1}^{n}(i-1) + \sigma(n-\tfrac{1}{2}),$$

where n denotes the index of a specific FLR 7, δ denotes a length parameter, σ denotes the width of the FLRs and wherein $X_n$ specifies the distance between the guard ring and the midpoint position of the FLR 7 with index n. This embodiment, that utilizes that the distances between FLRs are incremented according to $X_n = \Delta_1 + \delta(n-1)$, provides an X-ray sensor with N spaced apart FLRs given a spatial distribution that ensures that the magnitude of electrical field peaks are well balanced over all the rings. Such balanced electrical field peaks will reduce the risks that the sensor will be damaged by high voltages, i.e., voltages exceeding the break through voltage of the sensor material and will at the same time enable a better use of the area occupied by the termination.

Below we will provide a number of exemplary embodiments of the proposed X-ray sensor. This embodiments are not to be construed as limiting the scope of the proposed technology.

A specific embodiment of the proposed technology that fulfills these criteria is provided by an X-ray sensor, wherein the length parameter δ is selected from the interval [1.05 μm, 1.30 μm].

According to another specific embodiment of the proposed technology that fulfills these criteria there is provided an X-ray sensor wherein the separation distance $\Delta_1$ is selected from the interval [5 μm, 10 μm].

The proposed technology provides, as was mentioned above, an X-ray sensor wherein a number N of individual FLRs are positioned to ensure a balanced electric field peak profile as illustrated in e.g., FIGS. 5 and 6. The proposed technology has been shown to be especially effective when the number N of FLRs is relatively small, i.e., when the number N of FLRs is selected from the interval 1≤N≤10.

According to a preferred embodiment of the proposed technology there is provided an X-ray sensor 1, wherein the number N of FLRs is selected from the interval 3≤N≤8

A particularly preferred embodiment of the proposed technology provides an X-ray sensor 1, wherein the number N of FLRs is given by N=6.

If still another constraint is fulfilled another preferred embodiment is obtained. Namely that the distance $\Delta_g$ between the guard and the detector element positioned closest to the guard, preferably should be smaller than the distance d between individual detector elements in the active sensor area, see FIG. 3. Such an embodiment provides an improved protection to the sensor since it will ensure that any breakdown will occur at the edge of the guard ring p-n junction prior to the breakdown at the edge of the detector element nearest to the guard. To this end there is provided an embodiment of the proposed X-ray sensor 1, wherein the distance $\Delta_g$ between the guard ring 5 and the closest detector diode 2 arranged on the surface region 3 is selected from the interval 10 μm≤$\Delta_g$≤100 μm, preferably from the interval 20 μm≤$\Delta_g$≤40 μm.

Figure 17:
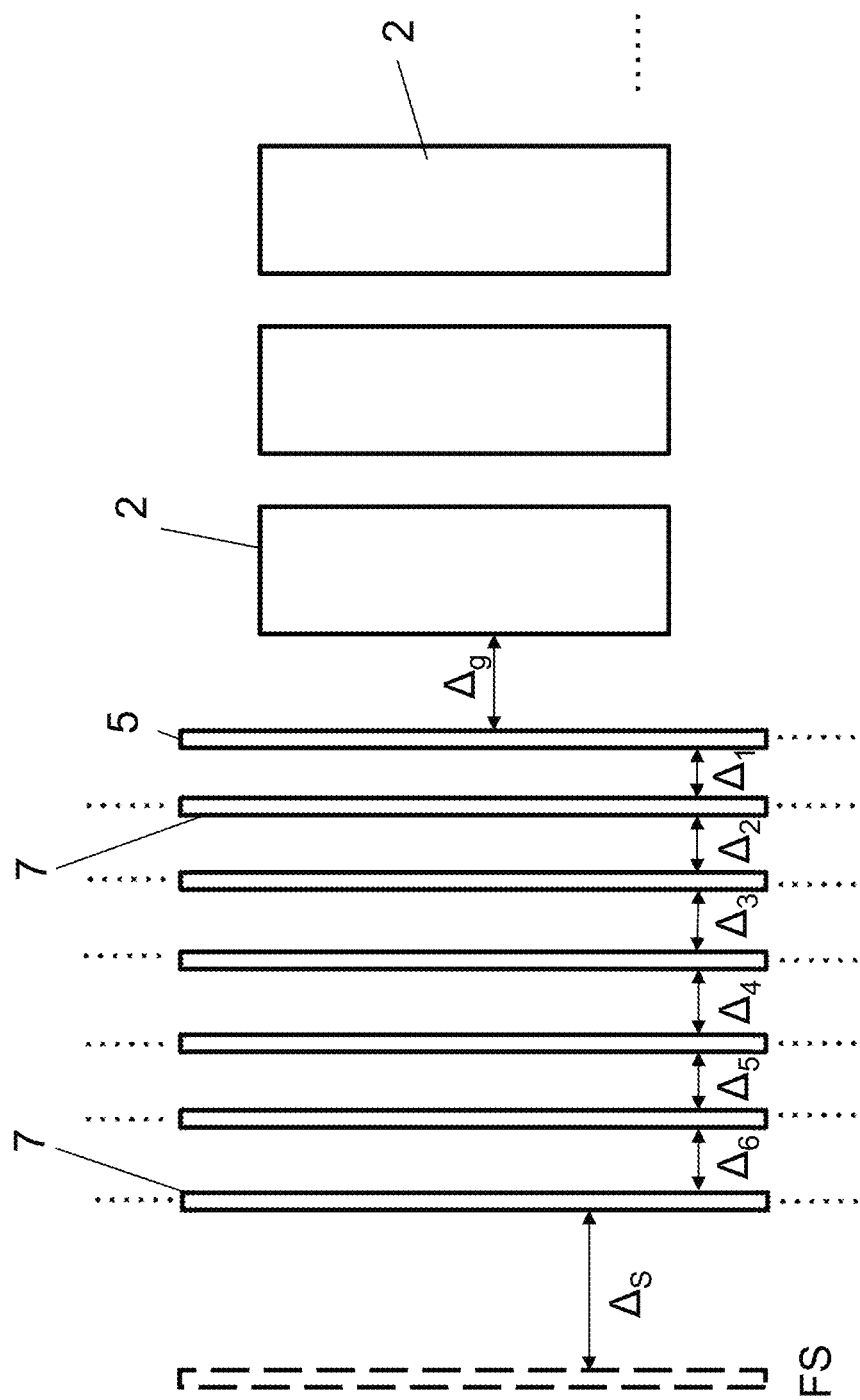
FIG. 17 is schematic diagram illustrating an example of an X-ray sensor seen from a top view according to an embodiment of the proposed technology.

In order to provide an explicit example of a sensor according to the proposed technology, reference is now made to FIG. 17. FIG. 17 provides a schematic top view of a section of a sensor as shown in FIG. 3. Note that distances in FIG. 17 are not to scale. The sensor comprises a number of detector diodes 2 surrounded by a guard ring 5 and six Field Limiting Rings, FLRs. An optional field stop denoted FS is also shown. According to the proposed technology different spacing's between the various rings should be selected. At first a guard ring 5 is arranged at a distance $\Delta_g$ from closest detector element. The distance $\Delta_g$ between the guard ring 5 and the closest detector diode 2 arranged on the surface region 3 is selected from the interval 10 μm≤$\Delta_g$≤100 μm, preferably from the interval 20 μm≤$\Delta_g$≤40 μm. Having arranged the guard ring 5 relative the detector element the next step is to arrange the plurality of Field Limiting Rings relative the guard ring. To this end distances between adjacent FLRs are selected from the intervals given in the following list:

$\Delta_1$, which is the distance between the first FLR and the guard ring 5, is selected from the interval [5 μm, 10 μm];

$\Delta_2$, which is the distance between the first FLR and the second FLR, is selected from the interval [6.05 μm, 11.3 μm];

$\Delta_3$, which is the distance between the second FLR and the third FLR, is selected from the interval [7.10 μm, 12.6 μm];

$\Delta_4$, which is the distance between the third FLR and the fourth FLR, is selected from the interval [8.15 μm, 13.9 μm];

$\Delta_5$, which is the distance between the fourth FLR and the fifth FLR, is selected from the interval [9.20 μm, 15.2 μm];

$\Delta_6$, which is the distance between the fifth FLR and the sixth FLR, is selected from the interval [10.25 μm, 16.5 μm].

The specific distances $\Delta_n$ are selected so that the distance between successive FLRs is either constant or increases with increasing n where n denotes the index of the FLRs, and 1≤n≤N. This implies in particular that if the first distance, the distance between the first FLR and the guard ring 5, is 10 μm, then the second distance $\Delta_2$, which is the distance between the first FLR and the second FLR, is selected from the interval [10 μm, 11.3 μm]. This in turn implies that the third distance $\Delta_3$, which is the distance between the second FLR and the third FLR, must be selected from the interval [10 μm, 12.6 μm] etc. If for example the second distance $\Delta_2$ is 11.1 μm, which lies in the interval [10 μm, 11.3 μm], the third distance has to be selected from the interval [11.1 μm, 12.6 μm] in order to ensure that the distance between successive FLRs is either constant or increases with increasing n where n denotes the index of the FLRs. Note that with these selections all the distances between adjacent FLRs lie within the effective area bounded by the lines α=(10+1.3×(n−1)) μm and β=(5+1.05×(n−1)) μm.

Optionally the distance $\Delta_s$, which is the distance between the sixth FLR and the Field Stop, FS, is selected from the interval [20 μm, 40 μm].

According to another optional embodiment of the proposed technology the width of the guard ring should be no less than about 20 μm and should preferably be no larger than around 100 μm. In other words, the proposed technology provides a X-ray sensor 1, wherein the width ω of the guard ring 5 is selected from the interval 20 μm≤ω≤100 μm, preferably the interval 25 μm≤ω≤55 μm, and even more preferably in the interval 45 μm≤ω≤55 μm, with a particularly preferred alternative given by 49 μm≤ω≤51 μm.

A particular embodiment of the proposed technology that fulfills the constraints of lying within the effective area and displaying distances between successive FLR that are either constant or increases with increasing n where n denotes the index of the FLRs is provided by specifying the positions of the FLRs relative the guard 5. This embodiment provides an X-ray sensor 1 having an active detector region comprising a plurality of detector diodes 2 arranged on a surface region 3 of the X-ray sensor 1. The X-ray sensor 1 further comprises a junction termination 4 surrounding the surface area 3 comprising the plurality of detector diodes 2. The junction termination 4 comprises a guard 5 arranged closest to the end of the surface region 3, a field stop 6 arranged outside the guard 5 and a number N of field limiting rings, FLRs 7, arranged between the guard 5 and the field stop 6. Each of the FLRs 7 are positioned so that their distances to the guard 5 is given by the formula $X_n = n\Delta_1 + \delta\Sigma_{i=1}^{n}(i-1) + \sigma(n-\frac{1}{2})$, where n denotes the index of a specific FLR 7, $\Delta_1$ is the distance between the guard and the midpoint position of the first FLR, closest to the guard 5, δ denotes a length parameter, σ denotes the width of the FLRs and $X_n$ specifies the distance between the guard ring and the midpoint position of the FLR 7 with index n.

The positions should, according to this particular example, be determined by the following functional form: $X_n = n\Delta_1 + \delta(\Sigma_{i=1}^{n}(i-1)) + \sigma(n-\frac{1}{2})$, where 1≤n≤N, $\Delta_1$ is a distance between the guard 5 and the midpoint position of the first FLR, δ denotes a length parameter, σ denotes the width of the FLRs and wherein $X_n$ specifies the distance between the guard ring and the midpoint position of an FLR 7 with index n, and where n denotes the index of a specific FLR 7. The parameters $\Delta_1$ and δ are to be selected from the intervals:

$$5 \text{ μm} \leq \Delta_1 \leq 10 \text{ μm}; 1.05 \text{ μm} \leq \delta \leq 1.30 \text{ μm}.$$

Let us illustrate this particular embodiment by looking at the distribution of N=3 FLRs relative the guard. Making use of the formula $X_n = n\Delta_1 + \delta(\Sigma_{i=1}^{n}(i-1)) + \sigma(n-\frac{1}{2})$, one obtains the positions of the FLRs as:

$$X_1 = \Delta_1 + 0 + \sigma \cdot \frac{1}{2}$$

$$X_2 = 2\cdot\Delta_1 + \delta\cdot 1 + \sigma\cdot 3/2$$

$$X_3 = 3\cdot\Delta_1 + \delta\cdot 3 + \sigma\cdot 5/2.$$

Choosing $\Delta_1 = 5$ μm, δ=1.05 μm and assuming a width σ of 6 μm one obtains the following three positions:

$$X_1 = 8 \text{ μm}$$

$$X_2 = 10 + 1.05 \text{ μm} + 9 \text{ μm} = 20.05 \text{ μm}$$

$$X_3 = 15 \text{ μm} + 3.15 \text{ μm} + 15 \text{ μm} = 33.15 \text{ μm}.$$

Figure 12:
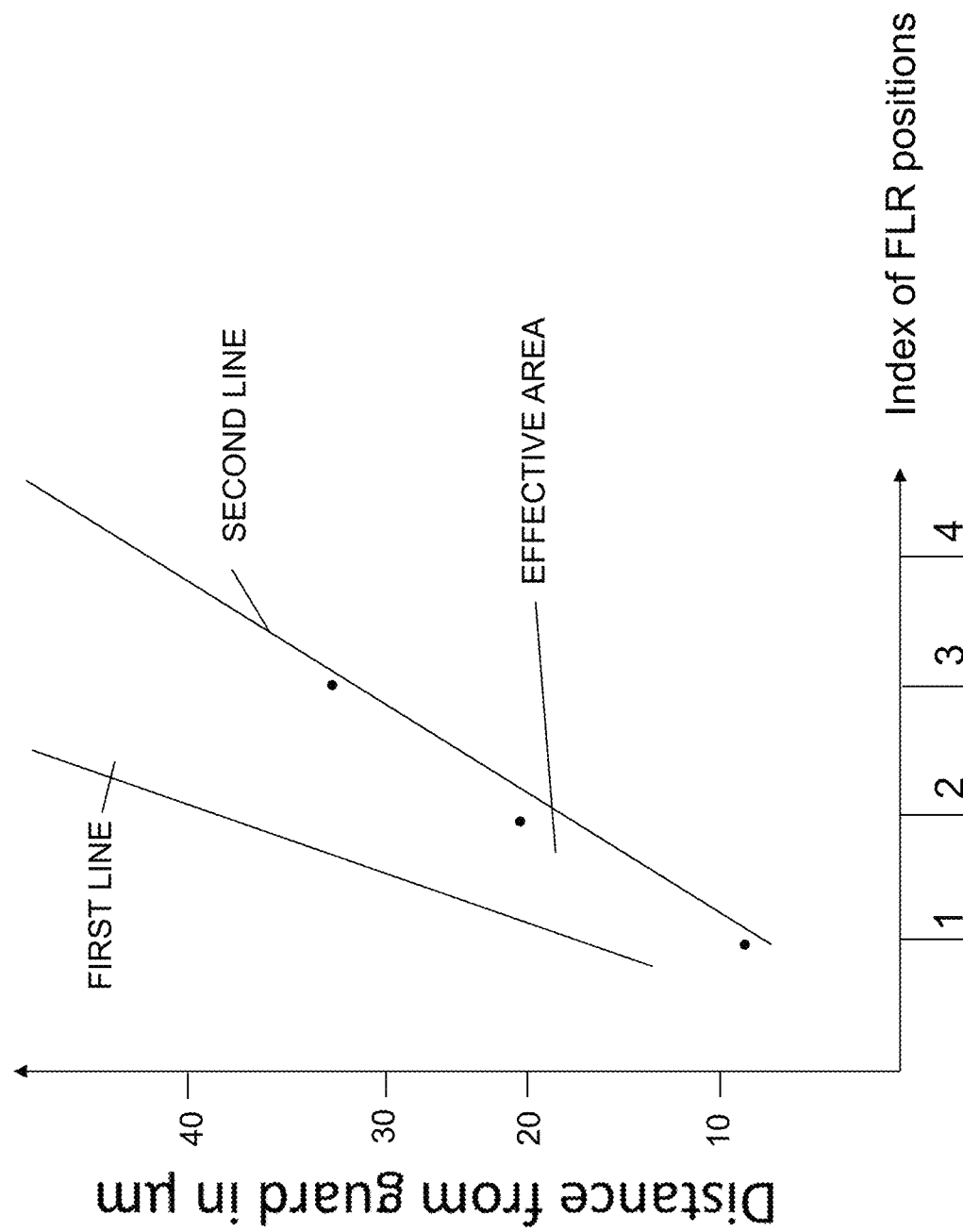
FIG. 12 is an exemplary graph providing an alternative illustration of the concept of an effective area. It is shown how distances between different FLRs and between the guard and the first FLR can be selected from points within the effective area.

The distribution is plotted in FIG. 12.

From the above numerical example it is clear that the individual distances between neighboring FLRs increases with increasing n. The points also falls within the effective area. FIG. 12 thus provides a schematic illustration of the effective area used to design such a sensor. FIG. 12, which is drawn for a constant FLR width of 6 μm, illustrates how a first FLR is placed at a location where there is a distance of 8 μm to the guard. The second FLR is placed at a position where there is a distance of 20.05 μm to the guard and the third FLR is placed at a location where there is a distance of 33.15 μm to the guard. The distances are defined as the distance between the outer end of the guard ring 5 and the center of the respective FLR. The dots are, as can be seen, all located within the area bounded by the two lines and the distance between adjacent or neighboring FLRs increases with the index n of the FLRs. This particular example only comprises three FLRs, it is however easy to add additional FLRs using the formula $X_n = n\Delta_1 + \delta(\Sigma_{i=1}^{n}(i-1)) + \sigma(n-\frac{1}{2})$, for larger values of n, one only needs to select a separation distance within the effective area and ensure that the distance from the neighboring FLR is larger or the same as the subsequent distance. It should be noted that all distances in this example and in the earlier refer to the shortest possible distance Δ between two neighboring FLRs. With this is intended the distance between the outer edge of the p-n junction belonging to the preceding FLR, outer meaning the one further away from the guard, and the inner edge of the p-n junction belonging to the consecutive FLR, inner edge meaning the edge being closer to the guard. This is illustrated in FIG. 9 where the distances $\Delta_1$, $\Delta_2$, $\Delta_3$, and $\Delta_4$ are all the shortest distances between the corresponding neighboring FLRs. It should also be noted that the partially enclosed area may be a completely enclosed area. To achieve this one generates at first the two mentioned lines, α and β, after that one generates a vertical line beginning at FLR index n=1, this bounds the area from below, and then generates a vertical line at FLR index n=N which bounds the area from above. Here the index n=N refers to the total number of FLRs that are to be used in the sensor.

In order to provide additional examples illustrating how the FLRs may be positioned reference is made FIG. 17. FIG. 17 provides a schematic top view of a section of a sensor as shown in FIG. 3. Note that distances in FIG. 17 are not to scale. The sensor comprises a plurality of detector diodes 2, a guard ring 5, six FLRs 7 and an optional field stop, denoted FS. In this particular example assume that each FLR 7 has a width extension σ. The positioning of the various FLRs 7 relative the guard ring 5 needs to know the width of a FLR 7. The proposed technology provides a sensor wherein the n different FLRs 7 are located at positions Xn as viewed from the guard ring 5. The positions Xn thus specifies distances between the guard ring 5 and the various FLRs 7, the distances are obtained as follows:

The center of the first FLR, with regard to its width dimension, has a distance to the guard ring 5 given by $X_1 = \Delta_1 + \sigma/2$. Here $\Delta_1$ is a length parameter selected from the interval [5 μm, 10 μm] and σ denotes the width of the FLR.

The center of second FLR, with regard to its width dimension, has a distance to the guard ring 5 given by $X_2 = X_1 + \Delta_2 + \sigma$. Here $\Delta_2$ is a length parameter selected from the interval [6.05 μm, 11.3 μm] with the constraint that $\Delta_2 \geq \Delta_1$. A particular example is given when $\Delta_2 > \Delta_1$.

The center of third FLR, with regard to its width dimension, has a distance to the guard ring 5 given by $X_3 = X_1 + X_2 + \Delta_3 + \sigma$. Here $\Delta_3$ is a length parameter selected from the interval [7.10 μm, 12.6 μm] with the constraint that $\Delta_3 \geq \Delta_2$. A particular example is given when $\Delta_3 > \Delta_2$.

The center of fourth FLR, with regard to its width dimension, has a distance to the guard ring 5 given by $X_4 = X_1 + X_2 + X_3 + \Delta_4 + \sigma$. Here $\Delta_4$ is a length parameter selected from the interval [8.15 μm, 13.9 μm] with the constraint that $\Delta_4 \geq \Delta_3$. A particular example is given when $\Delta_4 > \Delta_3$.

The center of fifth FLR, with regard to its width dimension, has a distance to the guard ring 5 given by $X_5 = X_1 + X_2 + X_3 + X_4 + \Delta_4 + \sigma$. Here $\Delta_5$ is a length parameter selected from the interval [9.20 µm, 15.2 µm], with the constraint that $\Delta_5 \geq \Delta_4$. A particular example is given when $\Delta_5 > \Delta_4$.

The center of sixth FLR, with regard to its width dimension, has a distance to the guard ring 5 given by $X_6 = X_1 + X_2 + X_3 + X_4 + X_4 + \Delta_5 + \sigma$. Here $\Delta_6$ is a length parameter selected from the interval $\Delta_6$, which is the distance between the fifth FLR and the sixth FLR, and is selected from the interval [10.25 µm, 16.5 µm] with the constraint that $\Delta_6 \geq \Delta_5$. A particular example is given when $\Delta_6 > \Delta_5$.

This particular sensor may moreover comprise a guard ring that is positioned at a distance $\Delta_g$ from closest detector element 2. The distance $\Delta_g$ between the guard ring 5 and the closest detector diode 2 arranged on the surface region 3 is selected from the interval 10 µm $\leq \Delta_g \leq$ 100 µm, preferably from the interval 20 µm $\leq \Delta_g \leq$ 40 µm. The sensor may optionally comprise a field stop, FS, located at a distance $\Delta_s$ from the sixth FLR where the distance $\Delta_s$ s selected from the interval [20 µm, 40 µm].

An alternative way to assign positions for the six FLRs in the example above utilizes the formula $X_n = n\Delta_1 + \delta(\Sigma_{i=1}^{n}(i-1)) + \sigma(n-\frac{1}{2})$, where $\Delta_1$ is a distance between the guard 5 and the midpoint position of the first FLR, $\delta$ denotes a length parameter, $\sigma$ denotes the width of the FLRs and wherein $X_n$ specifies the distance between the guard ring and the midpoint position of an FLR 7 with index n.

Using the formula stated above, the positions relative the guard for the six FLRs can be generated as:

$$X_1 = \Delta_1 + 0 + \sigma \cdot \frac{1}{2}$$

$$X_2 = 2 \cdot \Delta_1 + \delta \cdot 1 + \sigma \cdot 3/2$$

$$X_3 = 3 \cdot \Delta_1 + \delta \cdot 3 + \sigma \cdot 5/2$$

$$X_4 = 4 \cdot \Delta_1 + \delta \cdot 6 + \sigma \cdot 7/2$$

$$X_5 = 5 \cdot \Delta_1 + \delta \cdot 10 + \sigma \cdot 9/2$$

$$X_6 = 6 \cdot \Delta_1 + \delta \cdot 15 + \sigma \cdot 11/2$$

It is now possible to achieve numerical values by measuring $\sigma$, the width of the FLRs, and selecting $\Delta_1$ and $\delta$ from the intervals:

$$5 \text{ µm} \leq \Delta_1 \leq 10 \text{ µm}; 1.05 \text{ µm} \leq \delta \leq 1.30 \text{ µm}.$$

Where the specific values are to be selected with the proviso that the distances between neighboring FLRs are either constant or increases with increasing n. This procedure will yield a family of possible distributions, each distribution corresponding to a particular selection of $\Delta_1$ and $\delta$. All of these distribution yields an X-ray sensor where the magnitude of the electrical field peaks are well balanced over all the rings.

The proposed technology provides an X-ray sensor that yields a balanced electric field peak profile and is especially suited for a small number of FLRs. This combination makes the X-ray sensor highly desirable. The design provides a more robust sensor since the risk of exposing the sensor for a voltage over the break-through voltage of the used material is reduced. The sensor enables at the same time the use of a smaller number of FLRs. This is a highly desired feature since the area spared by reducing the number of FLRs can be used as a detection area. This will in turn improve the overall quality of the output from the sensor.

The proposed technology is also particularly well suited for sensors where the doping concentration is rather low. It is in particular well suited for an X-ray sensor, wherein the active detector region comprises a doped material having a doping concentration in the interval: $1 \times 10^{10}$ cm$^{-3}$ to $1 \times 10^{12}$ cm$^{-3}$.

Another specific embodiment of the proposed technology provides an X-ray sensor wherein the active detector region comprises a doped material, such as silicon, having the opposite type of doping as the field limiting rings, i.e., if the active detector region comprises a material of n-type doping, the FLRs are doped with a p-type doping.

According to an optional embodiment of the proposed technology the distance $\Delta_S$ between the last of the FLRs, i.e., the FLR with index N in case N FLRs are used, and the field stop 6 should preferable be in the range 20-40 µm. There is however a larger freedom in choosing the distance $\Delta_S$ and these particular embodiments are therefore optional.

Having described various embodiments of the proposed X-ray sensor below there will now be described a particular method for constructing such an X-ray sensor.

Figure 18:
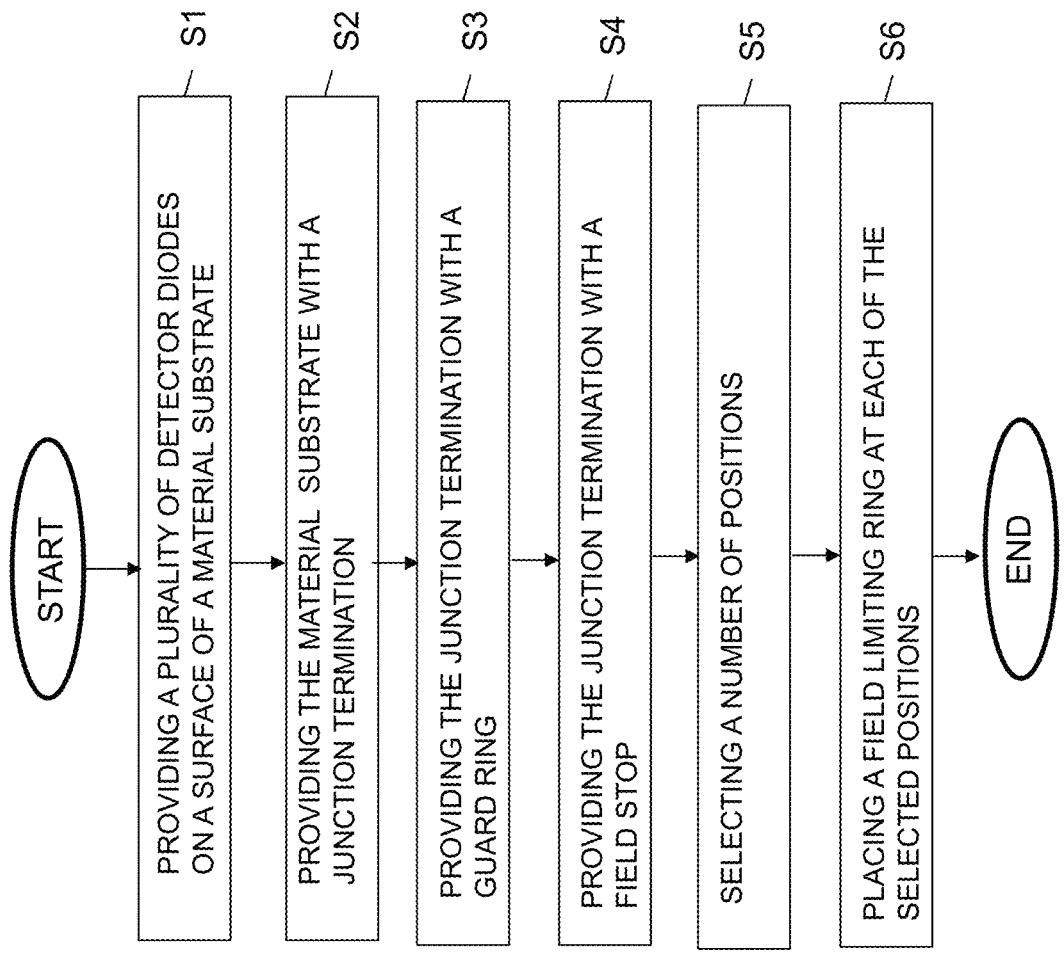
FIG. 18 is a schematic flow diagram illustrating a method for constructing an X-ray sensor according to the proposed technology.

According to this particular aspect, as shown in FIG. 18, the proposed technology provides a method for constructing an X-ray sensor 1. The method comprises the step of providing S1 a plurality of detector diodes on a surface region of a material substrate. The method also comprises providing S2 the material substrate with a junction termination surrounding the surface region. The junction termination is constructed by:
  providing S3 a guard ring adjacent the surface region, and
  providing S4 a field stop outside of the guard ring, and
  selecting S5 a number N of positions, the positions being selected so that distances between different FLRs 7 and between the guard and the first FLR_fulfills the following constraints:
  the distances lie within an effective area bounded by the lines $\alpha = (10 + 1.3 \times (n-1))$ µm and $\beta = (5 + 1.05 \times (n-1))$ µm, and
  the distance between successive FLRs 7 increases, or is the same, with increasing n where n denotes the index of the positions and $1 \leq n \leq N$.

The method also comprises placing S6 a field limiting ring, FLR, at each of the selected positions.

According to a particular embodiment of the proposed technology there is provided a method, wherein the step S5 of selecting a number N of positions comprises to select a distance $\Delta_1$ as the distance between the guard 5 and the midpoint position of the first FLR and select the positions of the N FLRs according to the formula $X_n = n\Delta_1 + \delta(\Sigma_{i=1}^{n}(i-1)) + \sigma(n-\frac{1}{2})$, where n denotes the index of a specific FLR 7, $\delta$ denotes a length parameter, $\sigma$ denotes the width of the FLRs and wherein $X_n$ specifies the distance between the guard ring and the midpoint position of an FLR 7 with index n.

The above embodiment takes into account the width dimension of the FLRs. The step of placing the FLRs at the selected position comprises to place the center points of the FLRs, with regard to the width dimension, at the selected positions.

According to another particular embodiment of the proposed technology there is provided a method, wherein the length parameter $\delta$ is selected from the interval [1.05 µm, 1.30 µm].

According to another particular embodiment of the proposed technology there is provided a method, wherein the separation distance $\Delta_1$ is selected from the interval [5 µm, 10 µm].

According to another particular embodiment of the proposed technology there is provided a method, wherein the number N of FLRs is selected from the interval $1 \leq N \leq 10$.

According to another particular embodiment of the proposed technology there is provided a method, wherein the number N of FLRs is selected from the interval $2 \leq N \leq 8$.

According to another particular embodiment of the proposed technology there is provided a method, wherein the number N of FLRs is given by N=6.

According to still another embodiment of the proposed technology there is provided a method, wherein the step S3 of providing a guard ring comprises to provide the guard at a distance $\Delta_g$ from the closest detector diode 2 arranged on the surface region 3, wherein the distance $\Delta_g$ is selected from the interval 10 $\mu m \leq \Delta_g \leq 100$ $\mu m$, preferably from the interval 20 $\mu m \leq \Delta_g \leq 40$ $\mu m$.

According to yet another embodiment of the proposed technology there is provided a method, wherein the step S3 of providing a guard ring comprises to provide a guard ring having a width $\omega$ that is selected from the interval 20 $\mu m \leq \omega \leq 100$ $\mu m$, preferably the interval 25 $\mu m \leq \omega \leq 55$ $\mu m$, even more preferably in the interval 45 $\mu m \leq \omega \leq 55$ $\mu m$, with a particularly preferred alternative given by 49 $\mu m \leq \omega \leq 51$ $\mu m$.

According to a particular embodiment of the proposed technology there is provided a method, wherein the step of providing S1 a plurality of detector diodes on a surface region of a material substrate comprises to provide the plurality of detector diodes on the surface region of a doped material substrate having a doping concentration in the interval $1 \times 10^{10}$ cm$^{-3}$ to $1 \times 10^{12}$ cm$^{-3}$.

According to a particular embodiment of the proposed technology there is provided a method, wherein the plurality of detector diodes are provided on a silicon substrate having a first type of doping, and wherein the step of placing S6 a field limiting ring, FLR, at each of the selected positions comprises placing a FLR of a second type of doping at each of the selected positions.

According to a particular embodiment of the proposed technology there is provided a method for constructing an X-ray sensor 1 comprising six Field Limiting Rings, FLRs. The method comprises the step of providing S1 a plurality of detector diodes 2 on a surface region of a material substrate, such as silicone. The method also comprises the step of providing S2 the material substrate with a junction termination surrounding the surface region. The junction termination is constructed by providing S3 a guard ring at the end of the surface region and by providing S4 a field stop outside of the guard ring. The junction termination is also constructed by selecting S5 six positions $X_i$, i=1, 2, 3 . . . 6. The positions are selected as follows:

The first position $X_1$ is selected at a distance to the guard ring 5 given by $X_1 = \Delta_1 + \sigma/2$. Here $\Delta_1$ is a length parameter selected from the interval [5 $\mu m$, 10 $\mu m$], and $\sigma$ is the width of a FLR.

The second position $X_2$ is selected to have a distance to the guard ring 5 given by $X_2 = X_1 + \Delta_2 + \sigma$. Here $\Delta_2$ is a length parameter selected from the interval [6.05 $\mu m$, 11.3 $\mu m$] with the constraint that $\Delta_2 \geq \Delta_1$, and $\sigma$ is the width of a FLR. A particular example relates to the case where $\Delta_2 > \Delta_1$.

The third position $X_3$ is selected to have a distance to the guard ring 5 given by $X_3 = X_1 + X_2 + \Delta_3 + \sigma$. Here $\Delta_3$ is a length parameter selected from the interval [7.10 $\mu m$, 12.6 $\mu m$] with the constraint that $\Delta_3 \geq \Delta_2$, and $\sigma$ is the width of a FLR. A particular example relates to the case where $\Delta_3 > \Delta_2$.

The fourth position $X_4$ is selected to have a distance to the guard ring 5 given by $X_4 = X_1 + X_2 + X_3 + \Delta_4 + \sigma$. Here $\Delta_4$ is a length parameter selected from the interval [8.15 $\mu m$, 13.9 $\mu m$] with the constraint that $\Delta_4 \geq \Delta_3$, and $\sigma$ is the width of a FLR. A particular example relates to the case where $\Delta_4 > \Delta_3$.

The fifth position $X_5$ is selected to have a distance to the guard ring 5 given by $X_5 = X_1 + X_2 + X_3 + X_4 + \Delta_4 + \sigma$. Here $\Delta_5$ is a length parameter selected from the interval [9.20 $\mu m$, 15.2 $\mu m$], with the constraint that $\Delta_5 \geq \Delta_4$, and $\sigma$ is the width of a FLR. A particular example relates to the case where $\Delta_5 > \Delta_4$.

The sixth position $X_6$ is selected to have a distance to the guard ring 5 given by $X_6 = X_1 + X_2 + X_3 + X_4 + X_4 + \Delta_6 + \sigma$. Here $\Delta_6$ is a length parameter selected from the interval [10.25 $\mu m$, 16.5 $\mu m$] with the constraint that $\Delta_6 \geq \Delta_6$, and $\sigma$ is the width of a FLR. A particular example relates to the case where $\Delta_6 > \Delta_5$.

The method also comprises the step of placing S6 a field limiting ring, FLR, at each of the selected positions.

The above embodiment takes into account the width dimension of the FLRs. The step of placing the FLRs at the selected position comprises to place the center points of the FLRs, i.e. the center point with regard to the width dimension of the FLR, at the selected positions.

The method may moreover comprise the step of providing the guard ring at a distance $\Delta_g$ from closest detector element 2. The distance $\Delta_g$ between the guard ring 5 and the closest detector diode 2 arranged on the surface region 3 is selected from the interval 10 $\mu m \leq \Delta_g \leq 100$ $\mu m$, preferably from the interval 20 $\mu m \leq \Delta_g \leq 40$ $\mu m$.

The method may optionally comprise the step of providing S4 a field stop at a distance $\Delta_s$ from the sixth FLR where the distance $\Delta_s$ Is selected from the interval [20 $\mu m$, 40 $\mu m$].

According to another aspect of the proposed technology there is provided an X-ray imaging system 100 that comprises an X-ray source 10 that is configured to emit X-rays. The X-ray imaging system 100 also comprises an X-ray detector system 20 that comprises at least one X-ray sensor 1 according to the proposed technology. The X-ray imaging system 100 also comprises an image processing device 30. Such an X-ray imaging system 100 is illustrated in FIG. 1.

As illustrated in FIG. 2, a detailed example of an X-ray imaging system 100 comprises an X-ray source 10, which emits X-rays; an X-ray detector system 20, which detects the X-rays after they have passed through the object; analog processing circuitry 25, which processes the raw electrical signal from the detector and digitizes it; digital processing circuitry 40 which may carry out further processing operations on the measured data such as applying corrections, storing it temporarily, or filtering; and a computer 50 which stores the processed data and may perform further post-processing and/or image reconstruction.

The overall detector may be regarded as the X-ray detector system 20, or the X-ray detector system 20 combined with the associated analog processing circuitry 25.

The digital part including the digital processing circuitry 40 and/or the computer 50 may be regarded as a digital image processing system 30, which performs image reconstruction based on the image data from the X-ray detector. The image processing system 30 may thus be seen as the computer 50, or alternatively the combined system of the digital processing circuitry 40 and the computer 50, or possibly the digital processing circuitry 40 by itself if the digital processing circuitry is further specialized also for image processing and/or reconstruction.

An example of a commonly used X-ray imaging system is a Computed Tomography (CT) system, which may include an X-ray source that produces a fan or cone beam of X-rays and an opposing X-ray detector system for registering the fraction of X-rays that are transmitted through a patient or object. The X-ray source and detector system are normally mounted in a gantry that rotates around the imaged object.

Accordingly, the X-ray source 10 and the X-ray detector system 20 illustrated in FIG. 2 may thus be arranged as part of a CT system, e.g. mountable in a CT gantry.

The invention claimed is:

1. An X-ray sensor, comprising:
    a surface region;
    an active detector region comprising a plurality of detector diodes arranged on the surface region; and a junction termination surrounding said surface region, said junction termination comprising;
        a guard arranged closest to an end of said surface region,
        a field stop arranged outside said guard, and
        a number N of field limiting rings (FLRs) arranged between said guard and said field stop, each of the number N of FLRs being positioned so that a distance between the guard and a first FIR of the number N of FLRs and distances between different FLRs of the number N of FLRS fulfill the following constraints:
            the distances lie within an effective area, said effective area being bounded by lines:
            $\alpha = (10 + 1.3 \times (n-1))$ µm and
            $\beta = (5 + 1.05 \times (n-1))$ µm, and
            a distance between successive FLRs of the number N of FLRs is either constant or increases with increasing n, where n denotes an index of the of the number N of FLRs, where $1 \le n \le N$.

2. The X-ray sensor according to claim 1, wherein the number N of FLRs are located at a distance from the guard according to $$X_n = n\Delta_1 + \Delta_1 + \delta(\Sigma_{i=1}^{n}(i-1)) + \sigma(n-\tfrac{1}{2}),$$

where n denotes an index of a specific FLR of the number N of FLRs, $\Delta_1$ is a distance between the guard and a midpoint position of the first FLR closest to the guard, $\delta$ denotes a length parameter, $\sigma$ denotes a width of the number N of FLRs, and $X_n$ specifies a distance between the guard and a midpoint position of an FLR of the number N of FLRs with index n.

3. The X-ray sensor according to claim 2, wherein the length parameter $\delta$ is selected from an interval [1.05 µm, 1.30 µm].

4. The X-ray sensor according to claim 2, wherein the distance $\Delta_1$ is selected from an interval [5 µm, 10 µm].

5. The X-ray sensor according to claim 1, wherein the number N is selected from an interval $1 \le N \le 10$.

6. The X-ray sensor according to claim 1, wherein the number N is selected from an interval $2 \le N \le 8$.

7. The X-ray sensor according to claim 1, wherein the number N is given by N = 6.

8. The X-ray sensor according to claim 1, wherein a distance $\Delta_g$ between the guard and a closest detector diode of the plurality of detector diodes arranged on the surface region is selected from an interval 10 µm $\le \Delta_g \le$ 100 µm.

9. The X-ray sensor according to claim 1, wherein a width ω of said guard is selected from an interval 20 µm $\le \omega \le$ 100 µm.

10. The X-ray sensor according to claim 1, wherein the active detector region comprises a doped material having a doping concentration in an interval $1 \times 10^{10}$ cm$^{-3}$ to $1 \times 10^{12}$ cm$^{-3}$.

11. The X-ray sensor according to claim 1, wherein the active detector region comprises a doped silicon having an opposite type of doping as the number N of FLRs.

12. An X-ray imaging system comprising:
    an X-ray source configured to emit X-rays;
    an X-ray detector system comprising at least one X-ray sensor according to claim 1; and
    an image processing device.

13. A method for constructing an X-ray sensor, said method comprising the steps of:
    providing a plurality of detector diodes on a surface region of a material substrate;
    providing said material substrate with a junction termination surrounding said surface region, said junction termination is constructed by:
    providing a guard ring adjacent said surface region,
    providing a field stop outside of said guard ring,
    selecting a number N of positions of N field limiting rings (FLRs) so that distances between the N FLRs and between the guard ring and a first FLR of the N FLRs fulfill the following constraints:
        the distances lie within an effective area bounded by lines:
        $\alpha = (10 + 1.3 \times (n-1))$ µm and
        $\beta = (5 + 1.05 \times (n-1))$ µm, and
        a distance between successive FLRs of the number N of FLRs is either constant or increases with increasing n, where n denotes an index of the number N of positions, and $1 \le n \le N$, and
    placing an FLR at each of said selected number N of positions.

14. The method according to claim 13, wherein the step of selecting a number N of positions of N FLRs comprises selecting a distance $\Delta_1$ as a distance between the guard ring and a midpoint position of the first FLR, and selecting the number N of positions of the N FLRs according to $$X_n = n\Delta_1 + \delta(\Sigma_{i=1}^{n}(i-1)) + \sigma(n-\tfrac{1}{2}))$$

where n denotes an index of a specific FLR of the N FLRs, $\delta$ denotes a length parameter, $\sigma$ denotes a width of the N FLRs, and $X_n$ specifies a distance between the guard ring and the midpoint position of an FLR of the N FLRs with index n.

15. The method according to claim 14, wherein the length parameter $\delta$ is selected from an interval [1.05 µm, 1.30 µm].

16. The method according to claim 14, wherein the distance $\Delta_1$ is selected from an interval [5 µm, 10 µm].

17. The method according to claim 13, wherein the number N is selected from an interval $1 \le N \le 10$.

18. The method according to claim 13, wherein the number N is selected from an interval $2 \le N \le 8$.

19. The method according to claim 13, wherein the number N is given by N = 6.

20. The method according to claim 13, wherein the step of providing a guard ring comprises providing said guard ring at a distance $\Delta_g$ from a closest detector diode of the plurality of detector diodes arranged on the surface region, wherein said distance $\Delta_g$ is selected from an interval 10 µm $\le \Delta_g \le$ 100 µm.

21. The method according to claim 13, wherein the step of providing a guard ring comprises providing a guard ring having a width ω that is selected from an interval 20 µm $\le \omega \le$ 100 µm.

22. The method according to claim 13, wherein the step of providing a plurality of detector diodes on a surface region of a material substrate comprises providing the plurality of detector diodes on the surface region of a doped material substrate having a doping concentration in an interval $1 \times 10^{10}$ cm$^{-3}$ to $1 \times 10^{12}$ cm$^{-3}$.

23. The method according to claim 22,
    wherein the material substrate comprises a silicon substrate having a first type of doping, and wherein the step of placing an FLR at each of said selected number N of positions comprises placing an FLR of a second type of doping at each of said selected number N of positions.

* * * * *